(12) United States Patent
Giacca et al.

(10) Patent No.: US 12,391,943 B2
(45) Date of Patent: Aug. 19, 2025

(54) MicroRNAs FOR CARDIAC REGENERATION THROUGH INDUCTION OF CARDIAC MYOCYTE PROLIFERATION

(71) Applicant: KING'S COLLEGE LONDON, London (GB)

(72) Inventors: Mauro Giacca, Trieste (IT); Serena Zacchigna, Trieste (IT); Miguel Luis Cunha Mano, Trieste (IT); Ana Sofia Bregieiro Eulalio, Trieste (IT)

(73) Assignee: KING'S COLLEGE LONDON, London (GB)

( * ) Notice: Subject to any disclaimer, the term of this patent is extended or adjusted under 35 U.S.C. 154(b) by 25 days.

(21) Appl. No.: 17/570,714

(22) Filed: Jan. 7, 2022

(65) Prior Publication Data
US 2022/0228143 A1 Jul. 21, 2022

Related U.S. Application Data

(62) Division of application No. 16/400,333, filed on May 1, 2019, now Pat. No. 11,236,332, which is a division of application No. 14/368,149, filed as application No. PCT/IB2012/057590 on Dec. 21, 2012, now Pat. No. 10,337,002.

(30) Foreign Application Priority Data

Dec. 23, 2011 (IT) .......................... RM2011A000685

(51) Int. Cl.
| | |
|---|---|
| *C12N 15/11* | (2006.01) |
| *C12N 5/077* | (2010.01) |
| *C12N 15/113* | (2010.01) |
| *G01N 33/50* | (2006.01) |
| *A61K 48/00* | (2006.01) |

(52) U.S. Cl.
CPC .......... *C12N 15/113* (2013.01); *C12N 5/0657* (2013.01); *G01N 33/5061* (2013.01); *A61K 48/00* (2013.01); *C12N 2310/141* (2013.01); *C12N 2320/30* (2013.01); *C12N 2501/65* (2013.01); *C12N 2506/02* (2013.01); *G01N 2500/10* (2013.01)

(58) Field of Classification Search
CPC ................. C12N 15/113; C12N 5/0657; C12N 2310/141; A61K 48/00
See application file for complete search history.

(56) References Cited

U.S. PATENT DOCUMENTS

| | | | |
|---|---|---|---|
| 10,337,002 B2 | 7/2019 | Giacca et al. | |
| 2005/0059005 A1 | 3/2005 | Tuschl et al. | |
| 2008/0171715 A1 | 7/2008 | Brown et al. | |
| 2008/0171716 A1 | 7/2008 | MacLachlan et al. | |
| 2008/0306017 A1 | 12/2008 | Croce et al. | |
| 2009/0281167 A1 | 11/2009 | Shen et al. | |
| 2009/0306181 A1 | 12/2009 | Ikeda et al. | |
| 2010/0124569 A1* | 5/2010 | Abbot ....................... A61P 7/00 424/484 |
| 2010/0197772 A1 | 8/2010 | Califano et al. | |
| 2012/0121697 A1 | 5/2012 | Rennard et al. | |
| 2012/0137379 A1 | 5/2012 | Gao et al. | |
| 2013/0005796 A1 | 1/2013 | Kawashimi et al. | |
| 2013/0150256 A1 | 6/2013 | Synnergren et al. | |
| 2015/0011609 A1 | 1/2015 | Giacca et al. | |
| 2019/0256850 A1 | 8/2019 | Giacca et al. | |

FOREIGN PATENT DOCUMENTS

| | | | |
|---|---|---|---|
| EP | 2446929 A1 | 5/2012 | |
| WO | WO-2007/148235 A2 | 12/2007 | |
| WO | WO-2009/099465 A2 | 8/2009 | |
| WO | WO-2009/105044 A1 | 8/2009 | |
| WO | WO-2010/081842 A2 | 7/2010 | |
| WO | WO-2010/120969 A1 | 10/2010 | |
| WO | WO-2010118979 A1 | 10/2010 | |
| WO | WO-2010/126355 A1 | 11/2010 | |
| WO | WO-2010/138263 A2 | 12/2010 | |
| WO | WO-2011/111824 | 9/2011 | |
| WO | WO-2013048734 A1 * | 4/2013 | ........... A61L 31/047 |

OTHER PUBLICATIONS

Ortega et al , Effects of miR-33 Deficiency on Metabolic and Cardiovascular Diseases: Implications for Therapeutic Intervention, International Journal of Molecular Sciences, 2023, 24, 10777: 1-18 (Year: 2023).*
Tu et al , Exosome-Derived From Sepsis Patients' Blood Promoted Pyroptosis of Cardiomyocytes by Regulating miR-885-5p/HMBOX1, Frontiers in Cardiovascular Medicine, 2022, vol. 9, 774193: 1-10 (Year: 2022).*
Melvin, et al., JAMA Special Edition, Mar. 3, 1975, 231:9 (951-959).
Reynolds, Trends in Cardio. Med., 24, 2014 (170-176).
National Heart, Lung, and Blood Institute (NHLBI), downloaded from https://www.nihilbi.nih.gov/health-topics/heart-attack, Jul. 13, 2018 (11 pages).
World Health Organization (WHO), Global Atlas on Cardiovascular Disease Prevention and Control, 2011, (166 pages).
Bergmann et al. "Evidence for cardiomyocyte renewal in humans" *Science* 324:98-102 (Apr. 2009).

(Continued)

*Primary Examiner* — Ekaterina Poliakova-Georgantas
(74) *Attorney, Agent, or Firm* — NIXON & VANDERHYE, PC

(57) ABSTRACT

The present invention discloses a set of human microRNAs, or a primary transcript for such microRNAs, or a precursor of such microRNAs or a mimic of such MicroRNAs or a combination thereof and their use as medicaments for inducing proliferation of cardiomyocytes for the prevention and treatment of heart, diseases associated with a loss of cardiomyocytes. The invention also relates to a method for screening microRNAs and biological and therapeutically active compounds for their ability to increase proliferation of cardiomyocytes.

18 Claims, 7 Drawing Sheets
Specification includes a Sequence Listing.

(56) References Cited

OTHER PUBLICATIONS

Eulalio et al. "Functional screening identifies miRNAs inducing cardiac regeneration" *Nature* 492:376-384 (Dec. 2012).

Landskroner-Eiger et al. "miRNAs as modulators of angiogenesis" *Cold Spring Harbor Persoectives in Medicine* 3:a006643, 13 paqes (Feb. 2013).

Paradis et al. "Endothelin-1 promotes cardiomyocyte terminal differentiation in the developing heart via heightened DNA methylation" *International Journal of Medical Science* 11:373-380 (Feb. 2014).

Zacchigna et al. "Adena-associated virus vectors as therapeutic and investigational tools in the cardiovascular system" *Circulation Research* 114: 1827-1846 (May 2014).

Aguirre et al. "In vivo activation of a conserved microRNA program induces mammalian heart regeneration" *Cell Stem Cell*, vol. 15, No. 5, pp. 589-604 (Nov. 2014).

Burton et al. "An intrinsic timer that controls cell-cycle withdrawal in cultured cardiac myocytes" *Developmental Biology*, vol. 216, No. 2, pp. 659-670 (Dec. 1999).

Cayrol et al. "Integrin avß3 acting as membrane receptor for thyroid hormones mediates angiogenesis in malignant T cells" *Blood*, vol. 125, No. 5, pp. 841-851 (Jan. 2015).

Chen et al. "Hypoxia-responsive miRNAs target argonaute 1 to promote angiogenesis" *Journal of Clinical Investiaation*, vol. 123, No. 3, pp. 1057-1067 (Mar. 2013).

Davis et al. "Nongenomic actions of thyroid hormone" *Nature Reviews Endocrinology*, vol. 12, No. 2, pp. 111-121 (Feb. 2016).

Ferrarini et al. "Adena-associated virus-mediated transduction of VEGF165 improves cardiac tissue viability and functional recovery after permanent coronary occlusion in conscious dogs" *Circulation Research*, vol. 98, No. 7, pp. 954-961 (Apr. 2006).

Kimura et al. "Hypoxia fate mapping identifies cycling cardiomyocytes in the adult heart" *Nature*, vol. 523, No. 7559, pp. 226-230 (Jul. 2015).

Lu et al. "EZH2 promotes angiogenesis through inhibition of miR-1/Endothelin-1 axis in nasopharyngeal carcinoma" *Oncotarget*, vol. 5, No. 22, pp. 11319-11332 (Nov. 2014).

Pepe et al. "Intramyocardial VEGF-B167 gene delivery delays the progression towards congestive failure in dogs with pacing-induced dilated cardiomyopathy" *Circulation Research*, vol. 106, No. 12, pp. 1893-1903 (Jun. 2010).

Zacchigna et al. "Bone marrow cells recruited through the neuropilin-1 receptor promote arterial formation at the sites of adult neoangiogenesis" *Jounal of Clinical Investigation*, vol. 118, No. 6, pp. 2062-2075 (Jun. 2008).

Zentilin et al. "Cardiomyocyte VEGFR-1 activation by VEGF-B induces compensatory hypertrophy and preserves cardiac function after myocardial infarction" *FASEB Journal*, vol. 24, No. 5, pp. 1467-1478 (May 2010).

Hu et al. "MicroRNA-210 as a novel therapy for treatment of ischemic heart disease" *Circulation* vol. 122 No. 11 suppl. 1, pp. S124-S131 (Sep. 2010).

Int'l Search Report for PCT/IB2012/057590, seven pages (May 2013).

Written Opinion for PCT/IB2012/057590, eight pages (May 2013).

Marquart et al., miR-33 links SREBP-2 induction to repression of sterol transporters, PNAS, vol. 107, No. 27, pp. 12228-12232, Jul. 6, 2010.

Najafi-Shoushtari et al., MicroRNA-33 and the SREBP Host Genes Cooperate to Control Cholesterol Homeostasis, Science, 328(5985), 9 pages, Jun. 18, 2010.

Rayner et al., MIR-33 Contributes to the Regulation of Cholesterol Homeostasis, Science, 328(5985), 9 pages, Jun. 18, 2010.

Torrini et al., Common Regulatory Pathways Mediate Activity of MicroRNAs Inducing Cardiomyocyte Proliferation, Cell Reports, 27, pp. 2759-2771, May 28, 2019.

\* cited by examiner

SEQUENCE LISTING

```
<160> NUMBER OF SEQ ID NOS: 36

<210> SEQ ID NO 1
<211> LENGTH: 23
<212> TYPE: RNA
<213> ORGANISM: Homo sapiens

<400> SEQUENCE: 1
acugcccuaa gugcuccuuc ugg                                              23

<210> SEQ ID NO 2
<211> LENGTH: 22
<212> TYPE: RNA
<213> ORGANISM: Homo sapiens

<400> SEQUENCE: 2
ugcccuaaau gccccuucug gc                                               22

<210> SEQ ID NO 3
<211> LENGTH: 22
<212> TYPE: RNA
<213> ORGANISM: Homo sapiens

<400> SEQUENCE: 3
aguuuugcau aguugcacua ca                                               22

<210> SEQ ID NO 4
<211> LENGTH: 22
<212> TYPE: RNA
<213> ORGANISM: Homo sapiens

<400> SEQUENCE: 4
aguuuugcag guuugcauuu ca                                               22

<210> SEQ ID NO 5
<211> LENGTH: 21
```

```
<212> TYPE: RNA
<213> ORGANISM: Homo sapiens

<400> SEQUENCE: 5
aucacauugc cagggauuuc c                                      21

<210> SEQ ID NO 6
<211> LENGTH: 21
<212> TYPE: RNA
<213> ORGANISM: Homo sapiens

<400> SEQUENCE: 6
aucacauugc cagggauuac c                                      21

<210> SEQ ID NO 7
<211> LENGTH: 21
<212> TYPE: RNA
<213> ORGANISM: Homo sapiens

<400> SEQUENCE: 7
uucaaguaau ucaggauagg u                                      21

<210> SEQ ID NO 8
<211> LENGTH: 22
<212> TYPE: RNA
<213> ORGANISM: Homo sapiens

<400> SEQUENCE: 8
cuuucagucg gauguuugca gc                                     22

<210> SEQ ID NO 9
<211> LENGTH: 22
<212> TYPE: RNA
<213> ORGANISM: Homo sapiens

<400> SEQUENCE: 9
cuuucagucg gauguuuaca gc                                     22

<210> SEQ ID NO 10
<211> LENGTH: 22
<212> TYPE: RNA
<213> ORGANISM: Homo sapiens

<400> SEQUENCE: 10
cagugccucg gcagugcagc cc                                     22

<210> SEQ ID NO 11
<211> LENGTH: 22
<212> TYPE: RNA
<213> ORGANISM: Homo sapiens

<400> SEQUENCE: 11
uucacauugu gcuacugucu gc                                     22

<210> SEQ ID NO 12
<211> LENGTH: 22
<212> TYPE: RNA
<213> ORGANISM: Homo sapiens

<400> SEQUENCE: 12
ggugcagugc ugcaucucug gu                                     22

<210> SEQ ID NO 13
```

```
<211> LENGTH: 23
<212> TYPE: RNA
<213> ORGANISM: Homo sapiens

<400> SEQUENCE: 13
aacauucaac gcugucggug agu                                              23

<210> SEQ ID NO 14
<211> LENGTH: 22
<212> TYPE: RNA
<213> ORGANISM: Homo sapiens

<400> SEQUENCE: 14
acaguagucu gcacauuggu ua                                               22

<210> SEQ ID NO 15
<211> LENGTH: 21
<212> TYPE: RNA
<213> ORGANISM: Homo sapiens

<400> SEQUENCE: 15
ugauugucca aacgcaauuc u                                                21

<210> SEQ ID NO 16
<211> LENGTH: 23
<212> TYPE: RNA
<213> ORGANISM: Homo sapiens

<400> SEQUENCE: 16
uaagugcuuc cauguuuugg uga                                              23

<210> SEQ ID NO 17
<211> LENGTH: 23
<212> TYPE: RNA
<213> ORGANISM: Homo sapiens

<400> SEQUENCE: 17
uaagugcuuc cauguuuuag uag                                              23

<210> SEQ ID NO 18
<211> LENGTH: 23
<212> TYPE: RNA
<213> ORGANISM: Homo sapiens

<400> SEQUENCE: 18
uaagugcuuc cauguuucag ugg                                              23

<210> SEQ ID NO 19
<211> LENGTH: 22
<212> TYPE: RNA
<213> ORGANISM: Homo sapiens

<400> SEQUENCE: 19
uuuaacaugg ggguaccugc ug                                               22

<210> SEQ ID NO 20
<211> LENGTH: 23
<212> TYPE: RNA
<213> ORGANISM: Homo sapiens

<400> SEQUENCE: 20
uaagugcuuc cauguuugag ugu                                              23
```

```
<210> SEQ ID NO 21
<211> LENGTH: 17
<212> TYPE: RNA
<213> ORGANISM: Homo sapiens

<400> SEQUENCE: 21
uaagugcuuc caugcuu                                                  17

<210> SEQ ID NO 22
<211> LENGTH: 22
<212> TYPE: RNA
<213> ORGANISM: Homo sapiens

<400> SEQUENCE: 22
uuuuucauua uugcuccuga cc                                            22

<210> SEQ ID NO 23
<211> LENGTH: 23
<212> TYPE: RNA
<213> ORGANISM: Homo sapiens

<400> SEQUENCE: 23
aaagugcugc gacauuugag cgu                                           23

<210> SEQ ID NO 24
<211> LENGTH: 22
<212> TYPE: RNA
<213> ORGANISM: Homo sapiens

<400> SEQUENCE: 24
uaugugccuu uggacuacau cg                                            22

<210> SEQ ID NO 25
<211> LENGTH: 21
<212> TYPE: RNA
<213> ORGANISM: Homo sapiens

<400> SEQUENCE: 25
gugucuuuug cucugcaguc a                                             21

<210> SEQ ID NO 26
<211> LENGTH: 22
<212> TYPE: RNA
<213> ORGANISM: Homo sapiens

<400> SEQUENCE: 26
aaagugcuuc ccuuuggacu gu                                            22

<210> SEQ ID NO 27
<211> LENGTH: 21
<212> TYPE: RNA
<213> ORGANISM: Homo sapiens

<400> SEQUENCE: 27
aaagugcuuc cuuuuagagg g                                             21

<210> SEQ ID NO 28
<211> LENGTH: 22
<212> TYPE: RNA
<213> ORGANISM: Homo sapiens

<400> SEQUENCE: 28
aaagugcuuc cuuuuagagg gu                                            22
```

```
<210> SEQ ID NO 29
<211> LENGTH: 21
<212> TYPE: RNA
<213> ORGANISM: Homo sapiens

<400> SEQUENCE: 29
uaauuuuaug uauaagcuag u                                              21

<210> SEQ ID NO 30
<211> LENGTH: 22
<212> TYPE: RNA
<213> ORGANISM: Homo sapiens

<400> SEQUENCE: 30
uauaccucag uuuuaucagg ug                                             22

<210> SEQ ID NO 31
<211> LENGTH: 22
<212> TYPE: RNA
<213> ORGANISM: Homo sapiens

<400> SEQUENCE: 31
uccauuacac uacccugccu cu                                             22

<210> SEQ ID NO 32
<211> LENGTH: 26
<212> TYPE: RNA
<213> ORGANISM: Homo sapiens

<400> SEQUENCE: 32
aaguaguugg uuuguaugag augguu                                         26

<210> SEQ ID NO 33
<211> LENGTH: 27
<212> TYPE: RNA
<213> ORGANISM: Homo sapiens

<400> SEQUENCE: 33
accuucuugu auaagcacug ugcuaaa                                        27

<210> SEQ ID NO 34
<211> LENGTH: 17
<212> TYPE: RNA
<213> ORGANISM: Homo sapiens

<400> SEQUENCE: 34
ucgccuccuc cucuccc                                                   17

<210> SEQ ID NO 35
<211> LENGTH: 18
<212> TYPE: RNA
<213> ORGANISM: Homo sapiens

<400> SEQUENCE: 35
uccagugccc uccucucc                                                  18

<210> SEQ ID NO 36
<211> LENGTH: 20
<212> TYPE: RNA
<213> ORGANISM: Homo sapiens
```

```
<400> SEQUENCE: 36
uguuuugaua acaguaaugu                                          20
```

MicroRNAs FOR CARDIAC REGENERATION THROUGH INDUCTION OF CARDIAC MYOCYTE PROLIFERATION

CROSS-REFERENCE TO RELATED APPLICATIONS

This application is a divisional of U.S. application Ser. No. 16/400,333, filed May 1, 2019, which is a divisional U.S. application Ser. No. 14/368,149, 371 (c) date Jun. 23, 2014, now U.S. Pat. No. 10,337,002, issued Jul. 2, 2019, which is a U.S. National Phase of International Application No. PCT/IB2012/057590, filed Dec. 21, 2012, which claims priority benefit of Italian Application No. RM2011A000685, filed Dec. 23, 2011, each of which is incorporated herein by reference.

Reference to Sequence Listing Submitted Electronically

The content of the electronically submitted sequence listing (Name: 8573_0004_Sequence_Listing.txt; Size: 5.35 kilobytes; and Date of Creation: Jan. 6, 2022) filed with the application is incorporated herein by reference in its entirety.

The present invention relates to the fields of pharmaceuticals and biotechnology. In particular, the present invention discloses a set of human microRNAs and their use as medicaments, especially as gene therapy, to induce proliferation of cardiomyocytes as a mean to stimulate cardiac regeneration for the treatment of heart diseases associated with a loss of cardiomyocytes (myocardial infarction, cardiomyopathy of ischemic and non-ischemic origin, myocarditis and heart failure).

In addition, the invention relates to a method for screening of biological and pharmaceutical active compounds for their ability to increase proliferation of cardiomyocytes.

BACKGROUND OF THE INVENTION

Despite the enormous progress made over the last several years in term of prevention and early diagnosis, epidemiological analysis in Western countries indicates that cardiovascular disorders are among the first causes of morbidity and mortality among people over 60 years. There are approximately 600,000 deaths/year in Europe from myocardial infarction and, even more relevant, heart failure is estimated to affect over 15 million people worldwide, representing one of the leading causes of death; this number is certainly going to increase as a consequence of the ageing of the global population and the improved medical technologies. Despite pharmacological treatment, long-term prognosis of heart failure patients remains poor: more than 60% of these patients die within 5 years, from a worsening of the disease or due to sudden ventricular arrhythmias. Up to 16% of patients are re-admitted to hospital within the first 6 months following their release, rendering this disease the most frequent cause of hospitalization (about 20%) in the population over 65 years of age.

In light of these considerations, the development of novel therapies having a direct impact on cardiac myocyte proliferation, viability and function, thus being collectively addressed at improving cardiac tissue maintenance and regeneration, are absolutely required.

In mammals, enlargement of the heart during embryonic development is primarily dependent on the increase in cardiomyocyte number, but shortly after birth cardiac myocytes stop proliferating and further growth of the myocardium occurs through hypertrophic enlargement of existing myocardial cells (Ahuja et al. 2007; van Amerongen and Engel 2008). This switch in the growth potential of cardiomyocytes occurs at different stages of development in different species: in the mouse, it occurs shortly after birth while in the rat between post-natal day 3 and 4; whereas human cardiomyocytes show a striking reduction in the proliferative capacity after 7 months of age. Recent evidences obtained by dating of cardiomyocyte DNA in humans has indicated that cardiomyocytes physiologically renew at a rate of 1% at the age of 25 and 0.45% at the age of 75, and that fewer than 50% of the cardiomyocytes are exchanged during the normal life span (Bergmann et al. 2009).

As a consequence of this limited proliferation capacity of adult cardiomyocytes, the ability of the mammalian adult heart to repair itself following injury is very restricted (Senyo et al. 2012). In particular, the loss of cardiomyocyte that occurs after various types of myocardial damage, typically after myocardial infarction, is not repaired by the generation of new contractile tissue but by the formation of a scar. This significantly compromises cardiac function, which often tends to worsen over time, leading to heart failure. Thus, the identification of novel means to promote the regeneration of contractile cardiac tissue after injury appears mandatory.

The transition of cardiomyocytes from a proliferative state, characteristic of embryonic stages, to the differentiated hypertrophic phenotype typical of adult cells is a highly regulated process, in which several cell cycle regulators, transcriptional factors, growth factors, cytokines and signaling pathways take part (Ahuja et al. 2007; van Amerongen and Engel 2008). However, the exact molecular mechanisms controlling this transition and those responsible for sustaining proliferation and differentiation of cardiac myocytes remain largely unknown.

MicroRNAs are evolutionarily conserved small noncoding RNAs that regulate gene expression at the post-transcriptional level. In animal cells, repression of gene expression by microRNAs is achieved by base-pairing to partially complementary sequences present mostly in 3' UTRs of target messenger RNAs (mRNAs), resulting in translation repression, mRNA degradation, or both (Eulalio et al. 2008). The microRNA seed sequence, essential for the binding of the microRNA to the mRNA, is a conserved sequence which is generally situated at positions 2-8 from the microRNA 5'-end (Filipowicz et al, 2008). Even though base pairing of microRNA and its target mRNA is not perfect, the region corresponding to the seed sequence has to be perfectly complementary. Thus the seed sequence is the primary specificity determinant for target selection. The small size of the seed sequence means that a single microRNA can regulate is many, even hundreds, different genes.

MicroRNAs are genome-encoded sequences generally transcribed by RNA polymerase II into primary microRNAs (pri-microRNAs). The pri-microRNAs are then sequentially processed by two endonucleases of the RNAse III family: in the nucleus, Drosha processes the pri-microRNA into a precursor microRNA (pre-microRNA) of approximately 60-80 nucleotides, after which the pre-microRNA is further processed, in the cytoplasm, by Dicer to form a duplex containing two strands, of about 19-23 nucleotides. The microRNA duplex is then unwound, and the mature microRNA is incorporated into the RNA-induced silencing complex (RISC), containing, among others, Argonaute and GW182 proteins essential for the silencing by microRNAs (reviewed in Ghildiyal and Zamore 2009), The reference repository of published microRNA sequences and associated annotations (miRBase; www.mirbase.org) in its release 18, Nov. 2011, contains 18226 entries representing hairpin precursor microRNAs expressing 21643 mature microRNA products in 168 species.

Taking into consideration that individual microRNAs can have hundreds of targets, it is predicted that roughly one third of the human transcriptome is regulated by microRNAs. Another layer of regulatory complexity is introduced by the fact that each mRNA can be targeted by multiple microRNAs (Bartel 2009).

Control of gene expression by microRNAs has been shown to play important roles in a broad range of biological processes including development, cellular differentiation, proliferation, apoptosis, metabolism and immune response (Bueno et al, 2008; Kedde and Agami 2008; O'Connell et al. 2010). In keeping with the notion that microRNAs play a crucial role in controlling gene expression, misregulation of microRNA expression has been correlated with several pathologies, including cancer (Croce 2009) and viral infections (Umbach and Cullen 2009), and research is beginning to unravel the role of microRNAs in cardiovascular diseases (van Rooij and Olson 2007; Latronico and Condorelli 2009; Williams et al, 2009; Small and Olson 2011).

In contrast to many cellular factors involved in disease, which are difficult to modulate therapeutically, microRNA levels can be easily modulated in vivo by using microRNA mimics (which surrogate microRNA action) and antimiRs (sequences complementary to the mature microRNA sequence that block their activity). In fact, the efficient use of antimiRs has been demonstrated in non-human primates (Elmen et al., 2008; Lanford et al., 2010), and these studies have been advanced to human clinical trials.

The importance of microRNA regulation in cardiomyocyte function was put in evidence by several studies in mice, in which enzymes required for microRNA biogenesis (Dicer and Dgcr8) have been knocked-out specifically in the heart (Chen et al. 2007; Rao et al. 2009). These studies demonstrated that post-natal impairment of the RNAi pathway in cardiac muscle tissue leads to premature death of the animals with signs of heart failure and cardiomyopathy (Chen et al. 2007; Rao et al. 2009).

Profiling of microRNAs from various types of cardiac pathologies demonstrate altered microRNA expression patterns (Ikeda et al., 2007; Matkovich et al., 2009; Thum et al., 2007; van Rooij et al., 2006), indicating that disease-associated microRNAs may constitute both a powerful diagnostic tool as well as a promising therapeutic approach to treat cardiac diseases. Specific microRNAs have been implicated in heart diseases, including cardiac hypertrophy (Callis et al., 2009; Care et al., 2007; Lin et al., 2009), heart failure (Callis et al., 2009; Care et al., 2007; van Rooij et al., 2007), cardiac arrhythmias (Callis et al., 2009; Yang et al., 2007), fibrosis (Thum et al., 2008; van Rooij et al., 2008) and metabolic disorders (Najafi-Shoushtari et al., 2010). Furthermore, specific microRNAs have been shown to be necessary and sufficient to induce heart pathologies by performing gain- and loss-of-function experiments (reviewed in: Huang et al., 2010; Small et al., 2010).

Only a few microRNAs have been so far clearly implicated in cardiomyocyte proliferation, including miR-1, miR-133 and, more recently, members of the miR-15 family. Overexpression of miR-1 in the embryonic heart was shown to inhibit cardiomyocyte proliferation, which was linked to the repression of Hand2, a transcription factor required for cardiac growth during embryogenesis (Zhao et al. 2005). miR-133 inhibits proliferation of cardiomyocytes through the repression of SRF and cyclin D2, two essential regulators of muscle cell differentiation (Liu et al. 2008). Finally, the miR-15 family was shown to regulate the post-natal mitotic arrest of mouse cardiomyocytes, through the down-regulation of the expression of Chek1 (Porrello et al. 2011). To date, no exhaustive search for microRNAs able to induce cardiac regeneration has been performed yet.

The prior art is rich of disclosures relating the use of microRNAs both as diagnostic markers and therapeutic agents.

An exemplary list of these patents is: WO2011133288; WO2012160551; US20120295963; WO2012149557; US20120270826; WO2012122447; EP2496711; WO2012119051; WO2012115885; US20120207741; EP2288703; EP2475372; WO2012094366; EP2474616; US20120165392; WO2012083004; EP2462228; WO2012072685; US20120137379; US20120128761; WO2012061810; WO2012052953; US20120093885; US20120088687; EP2425016; US20120053227; US20120053333; WO2012020308; WO2012020307; WO2012012870; WO2012010905; EP2401365; WO2011157294; US20110262928; WO2011133036; EP2377559; CA2795776; WO2011112732; US20110160290; US20110160285; US20110152352; US20110144914; EP2322616; US20110086353; US20110086348; EP2305810; US20110003704; EP2257625; EP2254586; US20100267804; EP2234483; EP2228444; US20100227325; EP2202309; U.S. Pat. No. 7,709,616; EP2179060; WO2010033871; US20100029003; US20090306181; US20090298910; US20090291131; US20090081640; US20080261908; US20080256072; US20050256072.

WO2011111824 discloses microRNAs that promote the proliferation of cardiomyocytes, in particular miR-148a, miR-148b, miR-152 and miR-373.

WO2006/107826 discloses microRNAs regulating the differentiation, proliferation and death of cardiac and skeletal muscles cells. They can be used as active agents to induce differentiation in progenitor cells, and their down-regulation permits the maintenance and expansion of progenitor cell population.

WO2008/063919 provides β-myosin microRNA and methods for reducing or inhibiting its expression in order to screen active agents modulating its expression and methods of diagnosis for risk of cardiovascular disorders.

WO2009/058818 identifies miR-21, that alters energy metabolism in cardiomyocytes, contributing to cardiac remodeling. Its inhibition is disclosed as a method of treating cardiac hypertrophy, heart failure and/or myocardial infarction.

US2010/0010073 discloses 29 sequences of microRNAs for the diagnosis, prophylaxis and/or treatment of heart diseases, such as myocardial infarction, heart failure, chronic heart failure and/or cardiac hypertrophy.

CN101643791 discloses microRNA-328 and the application of an antisense thereof for diagnosing and controlling heart diseases. The antisense nucleotide has preventive and therapeutical effects.

WO2010/117860 discloses microRNA signature to predict prognosis in heart failure. The microRNAs are hsa-miR-367, hsa-miR-10a, hsa-miR-187, hsa-miR-452, hsa-miR-218, hsa-miR-10b, hsa-miR-214, hsa-miR-193a and hsa-miR-565.

WO2010/129950 discloses a method of treating or preventing pathologic cardiac hypertrophy, cardiac remodeling, myocardial infarction or heart failure by inhibiting the expression or activity of miR-451 in heart cells.

US20120165392 discloses a method for the treatment of cardiovascular diseases by modulating the expression of certain microRNAs by administering either an inhibitor or an agonist, as the case may be. EP2425016 discloses a similar method, wherein an inhibitor is administered or a functional microRNA. WO2012020308 and WO2012020307 disclose a method for treating acute tissue damage by administering a cell population or microvesicles capable of inducing tissue repair. These cells express a considerable number of heterogeneous proteins and microRNAs. For example, PDPC cells are indicated for cardiac ischemic damage, but there is no specific connection between individual microRNA and cardiac regeneration; these very heterogenous expressed factors and microRNAs are therefore to be considered as markers of cell identity rather than specific therapeutic agents.

EP2228444 discloses some microRNAs for use in the treatment of cardiovascular diseases, specifically hypertrophic diseases. These microRNAs induce a phenotypic change of cardiac myocyte size with the scope of reshaping the hypertrophic heart.

Other references from the above list refer to diseases different from cardiovascular diseases or to the profiling of microRNA for diagnosis of a cardiovascular disease; some microRNAs are shown as targets for therapeutic inhibitors.

However, there is no explicit disclosure of microRNAs that were specifically selected for their capacity of stimulating the proliferation of adult cardiomyocytes in the cardiac tissue which is damaged or impaired in its physiological function, thus permitting cardiac regeneration in vivo.

There is still the need to find effective ways of treating cardiovascular diseases, in particular those associated with a loss of cardiomyocytes (in particular, as consequences of myocardial infarction, cardiomyopathy of ischemic and non-ischemic origin, myocarditis and heart failure).

In particular, it is of extreme importance the discovery of active agents capable of stimulating the proliferation of cardiomyocytes, especially in the part of the cardiac tissue which is damaged or impaired in its physiological function, thus specifically permitting cardiac regeneration in vivo.

WO2010/138263 discloses microRNAs which can be delivered, using adeno-associated virus (AAV), to a target tissue, where heart is mentioned in a long list of possible target tissues. Hsa-miR-210 and hsa-miR-590-3p are disclosed in said document. The two microRNAs are part of a very long list. No specific enabling disclosure is given for any of the listed microRNAs for any of the listed target tissues. Moreover, no specific relation is made with any of the listed microRNAs with any of the listed target tissues. There is not explicit, unambiguous and enabling disclosure that hsa-mill-210 and hsa-miR-590-3p are useful for stimulating heart regeneration through cardiac myocyte proliferation.

MicroRNA-210 is disclosed as expressed in cardiomyocytes and capable of upregulating several angiogenic factors and prevent cell apoptosis and its usefulness in the treatment of myocardial infarction and ischemic heart diseases (Hu et al., 2010). The person skilled in the art knows that upregulating angiogenic factors and preventing cell apoptosis are useful mechanisms in acute phase of infarction, but are of less or no utility in long lasting situations of heart disease where a regeneration of cardiomyocyte is needed. In this context, the skilled person, a medical doctor expert in cardiology, is well aware of the different clinical significance between a therapy based on promoting angiogenesis and preventing cell apoptosis, this therapy is suitable for treating acute phases of cardiovascular diseases, such as myocardial infarction, and a therapy based on cardiomyocyte regeneration, such as the consequences of myocardial infarction, ischemic and non-ischemic cardiomyopathy, myocarditis and heart failure. This person is also aware that the therapy for the treatment of acute phase is unsuitable for the treatment of heart diseases where cardiomyocyte proliferation is necessary for heart regeneration.

It has now been found that 208 human microRNAs are able to significantly increase proliferation of rat cardiomyocytes in vitro, Of these, 36 microRNAs also increased proliferation of cardiomyocytes isolated from neonatal mouse hearts and of human stem cell derived cardiomyocytes.

In addition, it has also been found that the selected microRNAs induce proliferation of cardiomyocytes in animal models, in particular after intracardiac injection of synthetic microRNAs in rats or intraperitoneal injection of adeno-associated vectors (AAV) expressing the microRNAs in the mouse. Of notice, these microRNAs ameliorate heart function in an animal model of myocardial infarction, induced by coronary artery ligation by the induction of cardiac regeneration.

These results, obtained in well assessed and accepted animal models allow the development of medicaments for the treatment of cardiac diseases in human subjects,

SUMMARY OF THE INVENTION

The objects of the present invention are specified in the appended claims, however, other objects and scopes of the invention will be apparent from the foregoing specification.

Objects of the present invention are:
i) MicroRNAs, in particular a group of 36 selected microRNAs, preferably of human origin endowed with the activity to stimulate proliferation of cardiac myocytes, therefore making available a method and a medicament for stimulating heart regeneration in vivo by stimulating cardiomyocyte proliferation, and hence a method, a medicament and compositions, vectors and formulations for its administration for the treatment of cardiac pathologies associated with loss of cardiac myocytes (in particular consequences of myocardial infarction, cardiomyopathy of ischemic or non-ischemic derivation, myocarditis and heart failure).
ii) MicroRNAs, preferably of human origin, in particular the same 36 microRNAs of item i), endowed with the capacity to stimulate cardiomyocytes proliferation in cell culture, and thus endowed with the capacity to improve the obtainment and expansion of cardiomyocytes from embryonic stem cells (obtained from embryo cultures, nuclear transfer and animal cloning, through the iPS cell technology or any other technology), or from adult tissues, with the ultimate purpose to stimulate the generation of cardiomyocytes for laboratory use (diagnosis of human disease) or in vivo clinical application (cardiac repair for the above mentioned applications).

The related methods are also objects of the present invention.
iii) The delivery methods for the above microRNAs for in vitro and in vivo applications. In particular, vectors, compositions and formulations are within the scope of the present invention.
iv) A method for high-throughput screening of biologically active compounds for their ability to increase proliferation of cardiomyocytes based on high-content microscopy, this method is herein used for the selection of the microRNAs that are also object of the present invention.

An object of the present invention is a method for stimulating heart regeneration through cardiac myocyte proliferation, in particular to a subject in need thereof, by administering a microRNA according to the present invention or a combination thereof.

In particular, the method relates to treatment of a cardiac pathology associated with loss of cardiac myocytes, for example consequences of myocardial infarction, ischemic and non-ischemic cardiomyopathy, myocarditis and heart failure.

In a preferred embodiment, said method is performed by means of gene therapy.

DESCRIPTION OF THE INVENTION

It is an object of the present invention human microRNAs, in particular of 36 individual human microRNAs, or mimics of such microRNAs, or precursors of such microRNAs, or primary transcripts of such microRNAs, or a combination thereof able to induce proliferation of cardiac myocytes from different origins (rat, mouse and human), as listed in Table 1.

TABLE 1

List of microRNAs inducing cardiac proliferation

| SEQ ID | Name | miRBase Accession # | Sequence |
| --- | --- | --- | --- |
| 1 | hsa-miR-18a* | MIMAT0002891 | ACUGCCCUAAGUGCUCCUUCUGG |
| 2 | hsa-miR-18b* | MIMAT0004751 | UGCCCUAAAUGCCCCUUCUGGC |
| 3 | hsa-miR-19a* | MIMAT0004490 | AGUUUUGCAUAGUUGCACUACA |
| 4 | hsa-miR-19b-2* | MIMAT0004492 | AGUUUUGCAGGUUUGCAUUUCA |
| 5 | hsa-miR-23a | MIMAT0000078 | AUCACAUUGCCAGGGAUUUCC |
| 6 | hsa-miR-23b | MIMAT0000418 | AUCACAUUGCCAGGGAUUACC |
| 7 | hsa-miR-26b | MIMAT0000083 | UUCAAGUAAUUCAGGAUAGGU |
| 8 | hsa-miR-30a* | MIMAT0000088 | CUUUCAGUCGGAUGUUUGCAGC |
| 9 | hsa-miR-30e* | MIMAT0000693 | CUUUCAGUCGGAUGUUUACAGC |
| 10 | hsa-miR-33b* | MIMAT0004811 | CAGUGCCUCGGCAGUGCAGCCC |
| 11 | hsa-miR-130a* | MIMAT0004593 | UUCACAUUGUGCUACUGUCUGC |
| 12 | hsa-miR-143* | MIMAT0004599 | GGUGCAGUGCUGCAUCUCUGGU |
| 13 | hsa-miR-181a | MIMAT0000256 | AACAUUCAACGCUGUCGGUGAGU |
| 14 | hsa-miR-199a-3p | MIMAT0000232 | ACAGUAGUCUGCACAUUGGUUA |
| 15 | hsa-miR-219-5p | MIMAT0000276 | UGAUUGUCCAAACGCAAUUCU |
| 16 | hsa-miR-302a | MIMAT0000684 | UAAGUGCUUCCAUGUUUUGGUGA |
| 17 | hsa-miR-302b | MIMAT0000715 | UAAGUGCUUCCAUGUUUUAGUAG |
| 18 | hsa-miR-302c | MIMAT0000717 | UAAGUGCUUCCAUGUUUCAGUGG |
| 19 | hsa-miR-302c* | MIMAT0000716 | UUUAACAUGGGGGUACCUGCUG |
| 20 | hsa-miR-302d | MIMAT0000718 | UAAGUGCUUCCAUGUUUGAGUGU |
| 21 | hsa-miR-302e | MIMAT0005931 | UAAGUGCUUCCAUGCUU |
| 22 | hsa-miR-335* | MIMAT0004703 | UUUUUCAUUAUUGCUCCUGACC |
| 23 | hsa-miR-372 | MIMAT0000724 | AAAGUGCUGCGACAUUUGAGCGU |
| 24 | hsa-miR-455-5p | MIMAT0003150 | UAUGUGCCUUUGGACUACAUCG |
| 25 | hsa-miR-511 | MIMAT0002808 | GUGUCUUUUGCUCUGCAGUCA |
| 26 | hsa-miR-520a-3p | MIMAT0002834 | AAAGUGCUUCCCUUUGGACUGU |
| 27 | hsa-miR-520b | MIMAT0002843 | AAAGUGCUUCCUUUUAGAGGG |
| 28 | hsa-miR-520c-3p | MIMAT0002846 | AAAGUGCUUCCUUUUAGAGGGU |
| 29 | hsa-miR-590-3p | MIMAT0004801 | UAAUUUUAUGUAUAAGCUAGU |

TABLE 1-continued

List of microRNAs inducing cardiac proliferation

| SEQ ID | Name | miRBase Accession # | Sequence |
|---|---|---|---|
| 30 | hsa-miR-875-5p | MIMAT0004922 | UAUACCUCAGUUUUAUCAGGUG |
| 31 | hsa-miR-885-5p | MIMAT0004947 | UCCAUUACACUACCCUGCCUCU |
| 32 | hsa-miR-1244 | MIMAT0005896 | AAGUAGUUGGUUUGUAUGAGAUGGUU |
| 33 | hsa-miR-1248 | MIMAT0005900 | ACCUUCUUGUAUAAGCACUGUGCUAAA |
| 34 | hsa-miR-1281 | MIMAT0005939 | UCGCCUCCUCCUCUCCC |
| 35 | hsa-miR-1825 | MIMAT0006765 | UCCAGUGCCCUCCUCUCC |
| 36 | hsa-miR-2052 | MIMAT0009977 | UGUUUUGAUAACAGUAAUGU |

It is another object of the present invention one of the above microRNAs, or a combination thereof, for use in the promotion of cardiomyocyte proliferation in vivo, in the treatment of cardiac pathologies associated with loss of cardiac myocytes (including but not limited to the consequences of myocardial infarction, ischemic and non-ischemic cardiomyopathy, myocarditis and heart failure) through the induction of cardiac regeneration.

An additional object of the present invention is one of the above microRNAs, or a combination thereof, for use in vitro or ex vivo in the promotion of cardiomyocyte proliferation and in the expansion of cardiomyocytes derived from embryonic stem (ES) cells, induced pluripotent (iPS) cells or stem cells obtained by other procedures, or of adult cardiomyocytes.

A further object of the present invention is a method for high-throughput screening of biological and therapeutically active compounds for their ability to increase proliferation of cardiomyocytes. Said method is used for the selection of the microRNAs that are also object of the present invention.

A further object of the present invention is an RNA stretch comprising one or a combination of the above described microRNAs. Said RNA stretch is obtained in vitro through cell-free transcription methods, is produced synthetically or is expressed in the cells upon transfer of the relative DNA coding sequence, or is introduced or expressed in the cells by administration of a plasmid, a viral or other type of vector, with the proviso that it is not a natural occurring RNA.

The present invention provides said RNA stretch for use as a medicament for stimulating heart regeneration through cardiac myocyte proliferation.

The present invention also provides one of the above microRNAs, or their combination, for use as a medicament.

Another object of the present invention is a pharmaceutical composition comprising one of the above microRNAs, or their combination, as active ingredients for the treatment of cardiac pathologies associated with loss of cardiac myocytes (including, but not limited, to the consequences of myocardial infarction, cardiomyopathy, myocarditis and heart failure).

Still another object of the present invention is an agent designed to increase the expression levels of one or more of the above microRNAs for the treatment of cardiac associated diseases. Said agent is a microRNA, a chemical compound, a pharmaceutical composition, a recombinant protein obtained in vitro, expressed in the cells upon transfer of the relative DNA sequence, or expressed in the cells by administration of a vector.

These and other objects of the invention will be disclosed in detail in the foregoing specification also by means of examples and Figures.

In the Figures:

FIG. 1 shows the results of screening for the induction of cardiomyocyte proliferation by microRNAs. Each dot indicates the effect on cardiomyocyte proliferation by the individual microRNAs in two identical experiments. Control microRNAs fall into the bottom box (dotted lines); the 36 microRNAs that are subject of this invention, are inside the upper box (number of proliferating, EdU+, Ki-67+ cardiomyocytes >35% up to 55%).

Figure 5:
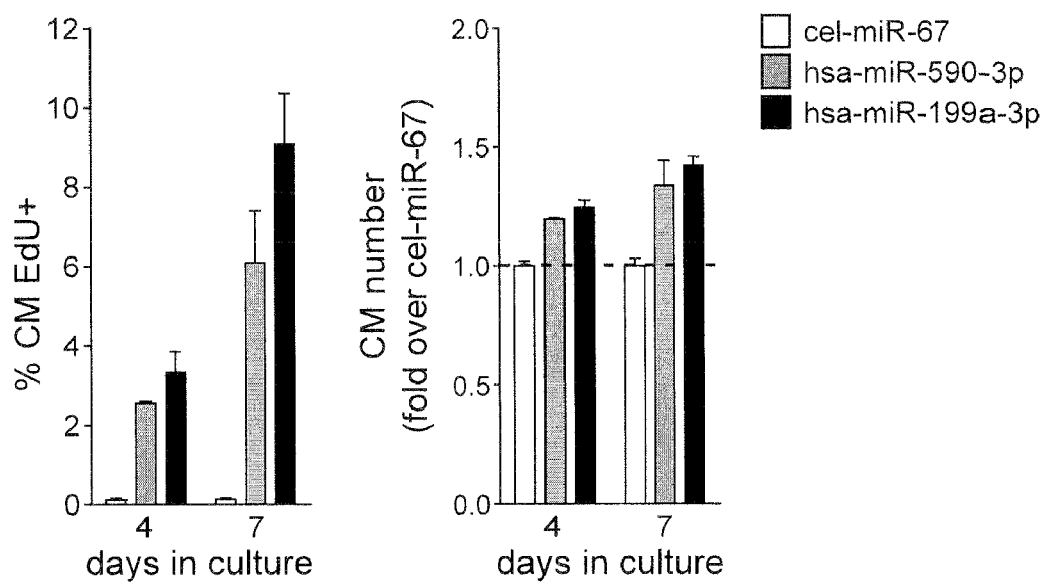

FIG. 5 shows examples of microRNAs (hsa-miR-590-3p and hsa-miR-199a-3p) increasing proliferation of fully differentiated rat cardiomyocytes ex vivo, isolated from adult (2-month old) animals, as evaluated by EdU positivity (left panel). Treatment with these microRNAs significantly increased the number of cardiomyocytes at 4 and 7 days after treatment (right panel). cel-miR-67 is an ineffective microRNA used as control.

Figure 6:
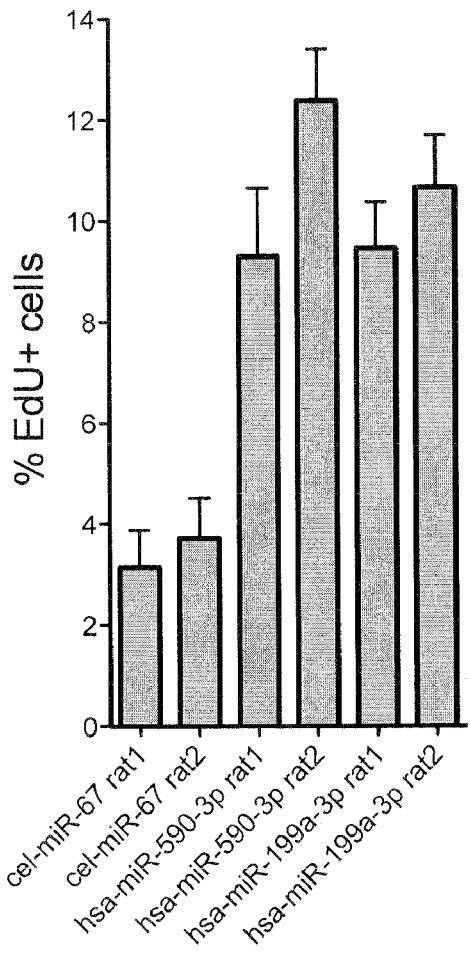

FIG. 6 shows examples of microRNAs increasing neonatal rat cardiomyocyte proliferation in vivo, as evaluated by EdU positivity in the treated hearts; cel-miR-67 is an ineffective microRNA used as control.

Figure 7:
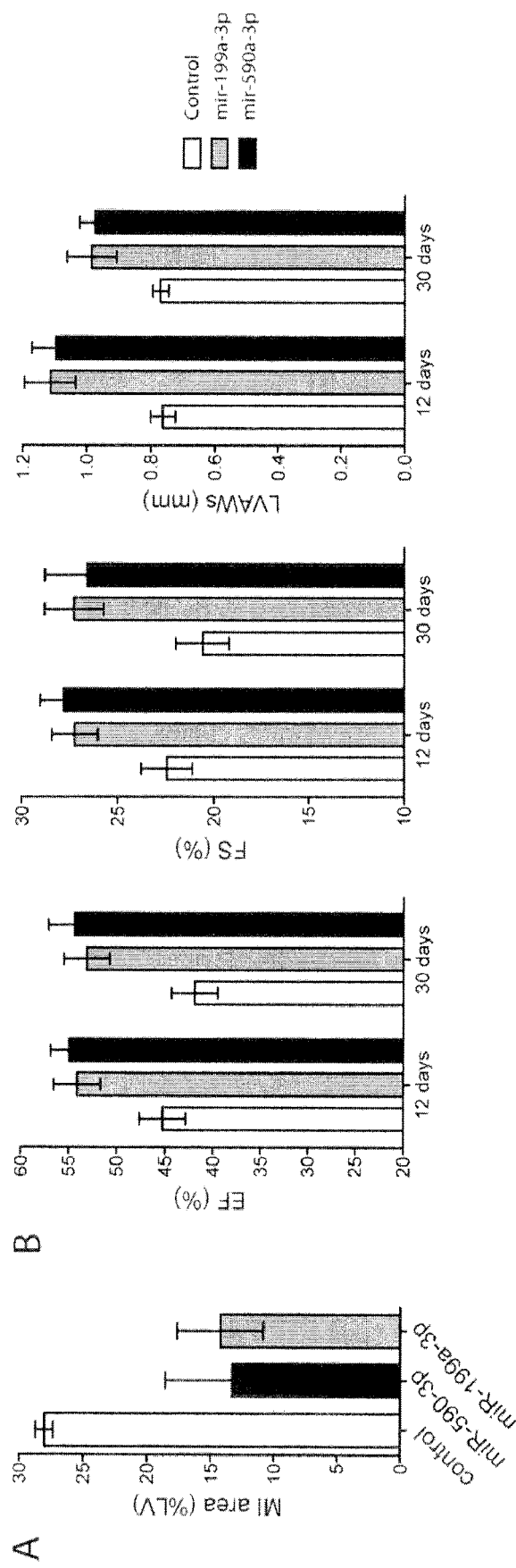

FIG. 7 shows the effects of microRNA hsa-miR-590-3p and microRNA hsa-miR-199a-3p upon delivery, using an AAV vector, to the heart of infarcted mice. A. Myocardial infarction (MI) area, B. From left to right, the histograms show: left ventricular ejection fraction (EF), left ventricular fractional shortening (FS) and left ventricular anterior wall systolic thickening (LVAWs) at days 12 and 30 after treatment. Controls are infarcted animals treated with an irrelevant microRNA.

DETAILED DESCRIPTION OF THE INVENTION

The present invention provides microRNAs, preferably of human origin, which have the property to induce proliferation of cardiomyocytes in vitro and in vivo and have been selected from a library through high throughput screening methods, in particular based on high content image analysis. Preferred method is fluorescence microscopy-based high-throughput screening in rat neonatal cardiomyocytes using synthetic microRNA mature sequences, corresponding to all the annotated human microRNAs (according to miRBase release 13.0, 2009).

The method object of the present invention for screening microRNAs, preferably of human origin, comprises:
a. obtaining a library of microRNA
b. transfecting each microRNA in a first cardiomyocyte isolated from a first animal subject;
c. cultivating said first transfected cardiomyocyte;
d. testing proliferation capacity of said first transfected cardiomyocyte;
e. selecting microRNAs capable of inducing proliferation in said first transfected cardiomyocyte;
f. transfecting each selected microRNA from step e) in a second cardiomyocyte isolated from a second animal subject of a species different from said first animal;
g. cultivating said second transfected cardiomyocyte,
h. testing proliferation capacity of said second transfected cardiomyocyte;
i. selecting microRNAs capable of inducing proliferation in said second transfected cardiomyocyte of step h).

In an embodiment of said method, after step i), the following steps are further provided:
j. transfecting each selected microRNA from step in a third cardiomyocyte previously isolated from a human subject;
k. cultivating said third transfected cardiomyocyte, testing proliferation capacity of said third transfected cardiomyocyte;
m. selecting microRNAs capable of inducing proliferation in said third transfected cardiomyocyte of step i), Preferably, in said selection step e), i) or m) at least one microRNA able to significantly increase cardiomyocyte proliferation by at least than 2-fold is selected.

Libraries useful for the present invention are available through commercial providers, for example Thermo Scientific, Sigma, Ambion.

As described in in more detail in Example 1, primary rat cardiomyocytes cells were treated with each of the microRNAs in the library, stained with a conventional nuclear dye, for example Hoechst 33432, antibodies against the cardiomyocyte marker sarcomeric alpha-actinin and the proliferation antigen Ki-67, and with EdU, a uridine analogue that is incorporated into newly synthesized DNA.

With this method, 208 microRNAs are identified, which can significantly increase cardiomyocyte proliferation.

Laboratory animals, for example rats, are used to isolate cardiac myocytes. Preferably, myocytes are isolated from neonatal animals according to well-known methods, Myocytes from ventricles are preferably used.

Individual microRNAs from the library are transferred to microwell plates, each one in an individual well, Subsequently, each of these microRNAs is transfected into animal cardiomyocytes. Preferred order of magnitude of seeded cells is $1 \times 10^4$ cells per well, A standard reverse transfection protocol can be used, at a suitable final concentration of microRNA, for example of 25 nM. Screening is repeated a number of times for accurate experimentation, for example in duplicate.

After transfection and cell seeding, for example twenty-four hours, culture medium can be replaced by fresh medium. Thereafter, as 28 h later, i.e. 52 h after plating, the culture medium is replaced with a proper medium to test cell vitality, at least two proliferation markers are used, for example EdU and Ki-67, for a suitable time (such as 20 h). Cells are fixed, usually around 72 h after plating, and processed for immunofluorescence as known in the art. Cells are then stained, preferably overnight at usual temperature (for example 4° C.) with primary antibodies diluted in blocking solution. Examples of primary antibodies are mouse monoclonal antibody against sarcomeric alpha-actinin, rabbit antibody against Ki-67. Other antibodies can be used. Cells are then washed with a medium, for example phosphate buffered saline and incubated for a sufficient time (such as 2 h) with the respective secondary antibodies conjugated to a detectable label. Cells are further processed to reveal EdU incorporation and stained as known in the art.

Image acquisition is then performed with commercial equipment, as high-content screening fluorescence microscope and image analysis is performed. Cells are scored as proliferating only if positive for both of the at least two proliferation markers; cardiomyocytes are distinguished from other cells present in the primary cultures (e.g. fibroblasts and endothelial cells) by their positivity for sarcomeric alpha-actinin.

The selection of microRNAs inducing cardiomyocyte proliferation is also repeated in adult cardiomyocyte cells. These are obtained preferably, but not exclusively, from the heart left ventricle using a standard procedure for the isolation of differentiated, adult cardiomyocytes. These are then treated with the said microRNAs; after treatment, proliferation of adult cardiomyocytes is verified by assessing positivity for different proliferation markers, such as EdU and Ki-67, as described for neonatal cardiomyocytes.

The selection of microRNAs is repeated in a laboratory animal different from the animal used in the first selection in order to screen those microRNAs that work by targeting a conserved set of targets.

The selection of microRNAs to increase cardiomyocyte proliferation in humans is then performed by transfecting the microRNAs resulting from the second selection on human cardiomyocytes derived from embryonic stem cells, which are available commercially (for example, Cytiva Cardiomyocytes from GE Healthcare). These cells comprise ventricular, atrial, and nodal subtypes, the majority being ventricular myocytes, and are characterized in terms of their morphology, electrophysiology and expression of cardiac markers, thus constituting a biologically relevant alternative to primary cells, which are difficult to obtain from human donors for predictive testing.

Collectively, the results described herein identify a subset of microRNAs able to increase proliferation of cardiac myocytes from different species, including is human cells, which are derived from embryonic cells, from neonatal individuals or from adult individuals. Of relevance, these microRNAs are the basis for the development of novel therapeutic approaches against cardiac diseases in humans, having the specific purpose to induce the regeneration of adult cardiac tissue by promoting cardiomyocyte proliferation.

Modifications of the methods above described which do not essentially modify the results achieved are within the boundaries of the present invention.

Other embodiments are herein presented.

It is a further object of the present invention a method for screening microRNAs, preferably of human origin, and microRNAs obtainable from the screening of a library of microRNAs, said screening comprising: a) transfecting each rnicroRNA in a cardiomyocyte isolated from a first animal subject, b) cultivating said transfected cardiomyocyte c) testing proliferation capacity of said transfected cardiomyocyte; d) selecting microRNAs capable of inducing proliferation in said transfected cardiomyocyte.

It is a further object of the present invention a method for screening microRNAs, preferably of human origin, and microRNAs obtainable from the screening of a library of microRNAs, said screening comprising: a) transfecting each microRNA in a cardiomyocyte isolated from a first animal subject, b) cultivating said transfected cardiomyocyte c) testing proliferation capacity of said transfected cardiomyocyte; d) selecting microRNAs capable of inducing proliferation in said transfected cardiomyocyte; e) transfecting each selected microRNA from step d) in a cardiomyocyte isolated from a second animal subject different from said first animal, f) cultivating said transfected cardiomyocyte, g) testing proliferation capacity of said transfected cardiomyocyte; h) selecting microRNAs capable of inducing proliferation in said transfected cardiomyocyte of step g).

It is a further object of the present invention a method for screening microRNAs, preferably of human origin, and microRNAs obtainable from the screening of a library of microRNAs, said screening comprising: a) transfecting each microRNA in a cardiomyocyte isolated from a first animal subject, b) cultivating said transfected cardiomyocyte c) testing proliferation capacity of said transfected cardiomyocyte; d) selecting microRNAs capable of inducing proliferation in said transfected cardiomyocyte; e) transfecting each selected microRNA from step d) in a cardiomyocyte isolated from a second animal subject different from said first animal, f) cultivating said transfected cardiomyocyte g) testing proliferation capacity of said transfected cardiomyocyte; h) selecting microRNAs capable of inducing proliferation in said transfected cardiomyocyte of step g), i) transfecting each selected microRNA from step h) in an isolated cardiomyocyte deriving from a human stem cell, j) cultivating said transfected cardiomyocyte, k) testing proliferation capacity of said transfected cardiomyocyte l) selecting microRNAs capable of inducing proliferation in said transfected cardiomyocyte of step k).

Steps of testing and selection in the above methods are preferably made with high throughput screening methods, in particular based on high content image analysis. Preferred method is fluorescence microscopy-based high-throughput screening.

The microRNAs obtained from the above method are capable of inducing proliferation in cardiomyocytes, in vitro and in vivo, in particular are capable of inducing proliferation of cardiomyocytes of an animal subject, more in particular in different animal subjects, even more in particular in humans.

The present invention also comprises primary transcripts, precursors and mimics of the microRNAs herein disclosed. The concepts of miRNA primary transcript, precursor and mimic are well-known in the art.

Modifications of microRNA backbone or synthetic nucleic acids anyhow mimicking natural microRNA function are also provided in the present invention. These modifications can be made according to well-known techniques, on condition that said modifications do not alter the function of the microRNAs of the present invention. Such modifications, include, but are not restricted to, substitution of non-bonding oxygen atoms in the phosphate group, introduction of an alkyl group in the sugar molecule of nucleotides, inclusion of extra bonds connecting carbon or oxygen atoms in the sugars of nucleotides (for example, the LNA technology), and the like. These modifications are well-known in the art and do not need specific further disclosure.

The microRNAs of the present invention are able to increase cardiac myocytes mitosis, cell division (cytokinesis) and cell number in vitro and in vivo, as demonstrated in the Examples below.

In the embodiments of the present invention relating the microRNAs as medicaments, in particular for the treatment of heart diseases associated with a loss of cardiomyocytes (consequences of myocardial infarction, cardiomyopathy of ischemic and non-ischemic origin, myocarditis and heart failure), they can be administered to a subject suffering from said disease by conventional methods with the specific objective of inducing cardiac regeneration by stimulating proliferation of cardiomyocytes.

Conveniently, said medicament is in the form of a preparation for parenteral, intracoronary, intravenous or intracardiac administration, but other forms are equally suitable for carrying out the present invention. The person skilled in the art will decide the effective time of administration, depending on the patient's conditions, degree of severity of the disease, response of the patient and any other clinical parameter within the general knowledge of this matter.

The pharmaceutical compositions will contain at least one of the following: synthetic RNA corresponding to the microRNA of the present invention or its primary transcript or precursor, DNA coding for said microRNA, DNA coding for a primary transcript or precursor for said RNA such as the microRNA is produced inside the cells containing this DNA. Administration of one of the microRNAs (or primary transcript or precursor) of the present invention or of the corresponding coding DNAs can be administered together with lipidic molecules such as cationic lipids, or peptides, or in the context of polymeric scaffolds, which can facilitate their delivery, according to the art. Another method to administer such microRNAs or their corresponding DNAs is by means of a suitable vector known for the administration of RNA or DNA. A more is preferred vector is the adeno-associated vector (AAV) of any capsid serotype, either natural (such as, but not restricted to, AAV1, AAV2, AAV8, AAV9) or artificial, a well-known viral vector for administration of DNA in vivo (Mingozzi et al. 2011). All these methods and formulation to administer the above synthetic RNA corresponding to the microRNA of the present invention, DNA coding for said microRNA, DNA coding for a primary transcript or precursor for said RNA such as the microRNA is produced inside the cells containing this DNA are conventional and well known in the art and do not need further explanation.

Injection is a preferred administration route, However, the skilled person in the art can decide to administer microRNAs by means of any conventional pharmaceutical composition. Reference can be made to Remington's Pharmaceutical Sciences, last edition.

The administration regime, dosage and posology will be determined by the physician according to his experience, the disease to be treated and the patient's conditions.

According to the administration route chosen, the compositions will be in solid or liquid form, suitable for oral, parenteral, intravenous or intra-arterial administration. Gene therapy is also another embodiment, The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

The active agents for use in the present invention can be administered as a medicament, i.e., a pharmaceutical composition. The composition contains at least one active agent of the present invention with a suitable carrier. A variety of administration routes and techniques may be utilized, among them parenteral techniques such as intravenous, intracardiac, and intra-arterial injections, catheterizations and the like. Average quantities of the active agent may vary and in particular should be based upon the recommendations and prescription of a qualified physician.

It is also an object of the present invention a method for the screening of biological and therapeutically active compounds for their ability to increase proliferation of cardiomyocytes, said method comprising the steps: a) providing a cardiomyocyte transfected with any of the above microRNA, b) bringing a candidate for a therapeutically active compound into contact with said cardiomyocyte, c) testing proliferation capacity of said transfected cardiomyocyte, d) selecting compounds capable of inducing proliferation of said transfected cardiomyocyte.

The following examples further illustrate the invention.

Example 1

Functional Screening Identifies MicroRNAs that Control Proliferation of Rat Neonatal Cardiomyocytes In Vitro Given the involvement of microRNAs in the regulation of several biological processes, including cell proliferation, we wanted to investigate whether microRNAs might control proliferation of primary cardiac myocytes ex vivo and identify the microRNAs most effective in increasing the proliferative capacity of these cells.

To tackle this issue, we performed a fluorescence microscopy-based high-throughput screening in rat neonatal cardiomyocytes using a commercial library of 988 microRNA mimics (miRIDIAN microRNA mimics, Dharmacon, Thermo Scientific) corresponding to all the annotated human microRNAs (according to miRBase release 13.0, 2009). Cells were stained with the nuclear dye Hoechst 33432, antibodies against the cardiomyocyte marker sarcorneric alpha-actinin and the proliferation antigen Ki-67, and with EdU, an uridine analogue that is incorporated into newly synthesized DNA. We used two proliferation markers (Ki-67 and EdU incorporation) to increase the reliability in the identification of proliferating cells; automated image analysis was performed on ca. 3000 cells per experimental condition.

Figure 1:
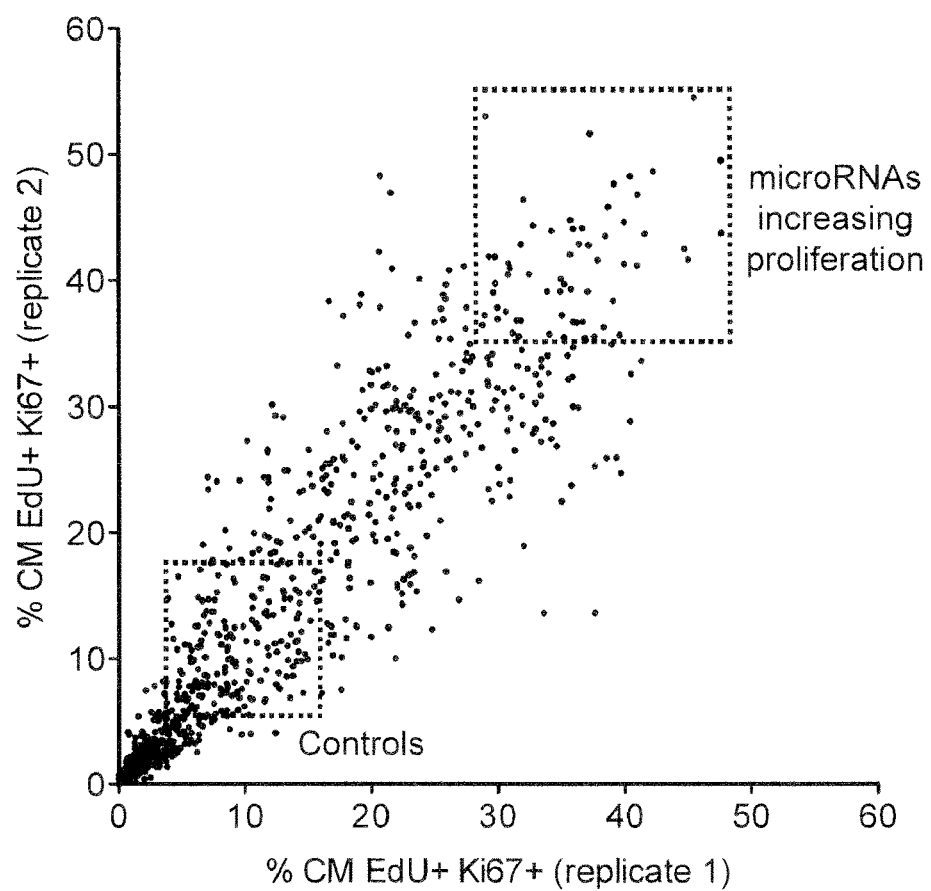

Using this approach, we identified 208 microRNAs able to significantly increase rat neonatal cardiomyocyte proliferation by more than 2-fold (from 12.5% basal proliferation up to more than 40%), FIG. 1 shows results of screening for the induction of cardiomyocyte proliferation by microRNAs. Each dot indicates the effect on cardiomyocyte proliferation by the individual microRNAs in two identical experiments. Control microRNAs fall into the bottom box (dotted lines); the 36 microRNAs that are subject of this invention, are inside the upper box (number of proliferating, EdU±, cardiomyocytes >35% up to 55%).

Figure 2:
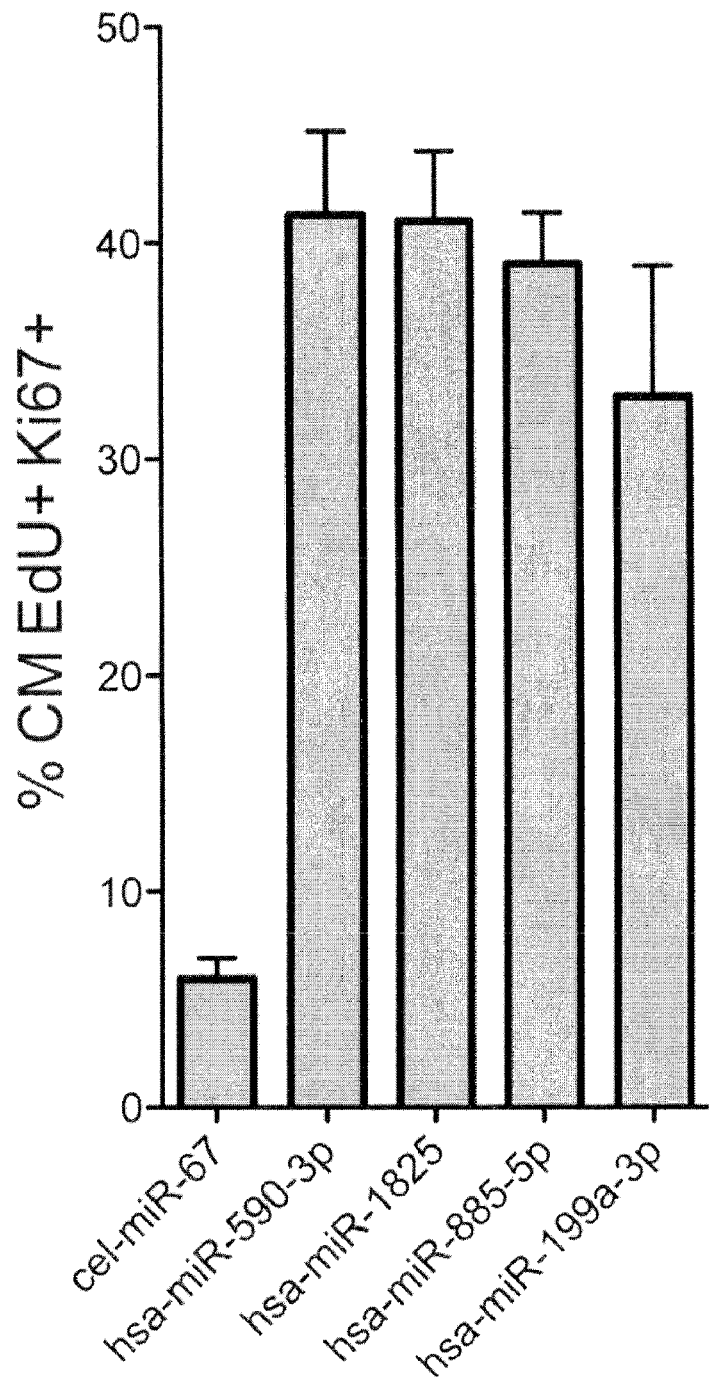
FIG. 2 shows examples of microRNAs increasing neonatal rat cardiomyocyte proliferation in vitro, as evaluated by EdU and Ki-67 positivity. cel-miR-67 is an ineffective microRNA used as control.

FIG. 2 shows examples of microRNAs increasing cardiomyocyte proliferation in vitro, as evaluated by EdU and Ki-67 positivity.

Methods

Animal care and treatments were conducted in conformity with institutional guidelines in compliance with national and international laws and policies (EEC Council Directive 86/609, OJL 358, Dec. 12, 1987).

Wistar rats were purchased from Charles River Laboratories Italia SrI. Cardiac myocytes from neonatal rats were isolated as described previously (Collesi et al. 2008), with minor modifications. In brief, ventricles from neonatal rats (day 0) were separated from the atria, cut into pieces and then dissociated in calcium and bicarbonate-free Hanks with HEPES (CBFHH) buffer containing 1.75 mg/ml trypsin (BD Difco) and 10 microg/ml DNase II (Sigma) under constant stirring. Digestion was performed at room temperature in eight to ten 10 min steps, collecting the supernatant to fetal bovine serum (FBS, Invitrogen) after each step. The supernatant was spun to isolate cells which were resuspended in Dulbecco's Modified Eagle Medium (DMEM) 4.5 g/l glucose (Invitrogen) supplemented with 5% FBS and 20 µg/ml vitamin 612 (Sigma). The collected cells were passed through a cell strainer (40 µm, BD Falcon) and then seeded onto uncoated 100 mm plastic dishes for 2 hours at 37° C. in 5% CO2 and humidified atmosphere. The supernatant, composed mostly of cardiomyocytes, was then collected, cells were counted and plated; cultures of neonatal rat ventricular cardiomyocytes prepared using this procedure have a purity of >90%.

The microRNA library corresponding to all the human mature microRNAs (miRIDIAN microRNA mimics), was obtained from Dharmacon, Thermo Scientific. Individual microRNAs were transferred robotically to Primaria 96 well plates (BD-Falcon) leaving columns 1 and 12 empty for addition of control microRNAs (cel-miR-67, hsa-miR-1). microRNAs were transfected into neonatal rat cardiomyocytes (1.0×10 cells were seeded per well), at a final concentration of 25 nM, through a standard reverse transfection protocol using Lipofectamine RNAimax transfection reagent (Invitrogen); screening was performed in duplicate.

Twenty-four hours after transfection and cell seeding, culture medium was replaced by fresh medium; 28 h later, i.e. 52 h after plating, the culture medium was replaced with medium containing 5 µM EdU for 20 h. Cells were fixed at 72 h after plating and processed for immunofluorescence. Briefly, cells were fixed with 4% paraformaldehyde for 15 min, permeabilized with 0.5% Triton X-100 in phosphate buffered saline solution (PBS) during 10 min, followed by 30 min blocking in 1% bovine serum albumin (BSA), Cells were then stained overnight at 4° C. with the following primary antibodies diluted in blocking solution: mouse monoclonal antibody against sarcomeric alpha-actinin (Abeam) and rabbit antibody against Ki-67 (Monosan). Cells were washed with PBS and incubated for 2 h with the respective secondary antibodies conjugated to Alexa Fluor 488 or 647 (Invitrogen). Cells were further processed using the Click-IT EdU555 Imaging kit (Invitrogen) to reveal EdU incorporation, according to the manufacturer's instructions, and stained with Hoechst 33432 (Invitrogen).

Image acquisition was performed using an ImageXpress Micro automated high-content screening fluorescence microscope (Molecular Devices) at a 10× magnification; a total of 16 images was acquired per wavelength, well and replicate, corresponding to ca. 3000 cells analyzed per condition. Image analysis was performed using the "Multi-Wavelength Cell Scoring" application module implemented in MetaXpress software (Molecular Devices). Cells were scored as proliferating only if positive for both proliferation markers (Ki-67 and EdU); cardiomyocytes were distinguished from other cells present in the primary cultures (e.g. fibroblasts and endothelial cells) by their positivity for sarcomeric alpha-actinin.

Example 2

A Subset of microRNAs Control In Vitro Proliferation of Cardiomyocytes from Different Organisms (Rat, Mouse and Human)

During development, cardiomyocytes in the mouse heart stop dividing sooner than their counterparts in the rat heart (shortly after birth and 3 to 4 days after birth, respectively). As a consequence of this, cardiamyocytes isolated from newborn mice have a proliferative capacity significantly lower than those isolated from rats of the same age; while proliferation of cardiomyocytes isolated from neonatal rats (post-natal day 0) is ca. 12.5%, that of mice cardiomyocytes is ca. 5%.

We therefore repeated the fluorescence microscopy-based high-throughput experiments described in Example 1 in mouse neonatal cardiomyocytes, using the 208 selected microRNAs that were shown to increase proliferation of rat cardiomyocytes. Results from these experiments showed that out of the 208 microRNAs tested, 36 microRNAs also increased the proliferation of mouse cardiomyocytes, suggesting that these may work by targeting a conserved set of targets.

Figure 3:
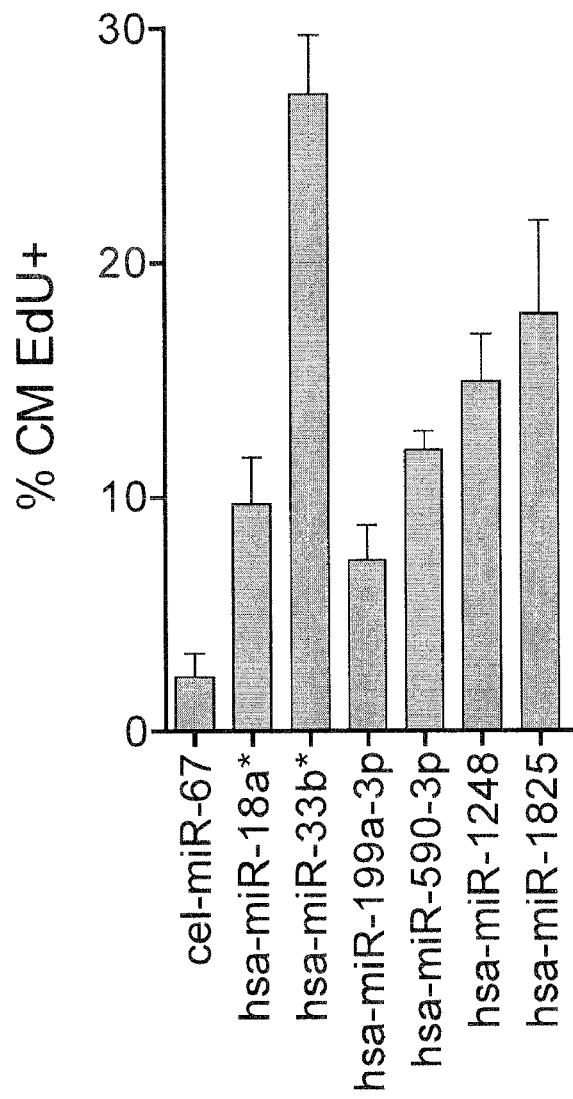
FIG. 3 shows examples of microRNAs increasing proliferation of cardiomyocytes derived from human embryonic stem cells (hESCs) in vitro, as evaluated by EdU positivity. cel-miR-67 is an ineffective microRNA used as control.

To assess the potential of applying microRNAs to increase cardiomyocyte proliferation in humans, we transfected the 36 microRNAs selected from the experiments performed in rat and mouse primary cardiomyocytes on human cardiomyocytes derived from embryonic stem cells (ESCs), which are available commercially (Cytiva Cardiomyocytes, GE Healthcare). These cells comprise ventricular, atrial, and nodal subtypes, the majority being ventricular myocytes, and have been extensively characterized in terms of their morphology, electrophysiology and expression of cardiac markers, thus constituting a biologically relevant alternative to primary cells, which are difficult to obtain from human donors for predictive testing. Results from these experiments demonstrated that treatment of human cardiomyocytes derived from embryonic stem cells with the selected microRNAs led to a very significant increase in cardiomyocyte proliferation (from ca. 3% up to ca, 30%); examples of microRNAs increasing the proliferation of ESC-derived human cardiomyocytes are shown in FIG. 3, Collectively, the results described herein identify a subset of 36 microRNAs able to increase proliferation of cardiac myocytes from different species, including human cells, These microRNAs are the basis for the development of novel therapeutic approaches against cardiac diseases in humans, specifically aimed at inducing the regeneration of cardiac tissue by stimulating the in vivo proliferation of cardiomyocytes.

Methods

CD1 mice were purchased from Charles River Laboratories Italia SrI. Mouse cardiomyocytes were isolated from newborn mice (post-natal day 0), as described in Example 1 for rat cardiomyocytes, Human embryonic stem cells (hESCs) derived cardiomyocytes (Cytiva Cardiomyocytes) were obtained from GE Healthcare. These cells have been extensively characterized and constitute therefore a relevant alternative to primary cells. Cells were thawed according to vendor's instructions.

Selected individual microRNAs were transferred robotically from microRNA library stock plates and re-arrayed onto collagen-coated black clear-bottom 96-well plates (Perkin-Elmer). Transfection of the selected microRNAs into mouse and human cells was performed as described in the Methods to Example 1, except that number of cells seeded per well was $1.5\times10^4$ and $1\times10^4$ for mouse and human cells, respectively, and final microRNA concentration was 50 nM and 25 nM for mouse and human cells, respectively.

Other reagents and procedures, including automated image acquisition and analysis, are the same as described in the Methods to Example 1, Example 3

MicroRNAs Increase Cardiac Myocytes Mitosis, Cell Division (Cytokinesis) and Cell Number In Vitro To demonstrate that the increase in cardiomyocyte proliferation, as assessed by staining with Ki-67 proliferation marker and EdU incorporation during DNA synthesis, correlates with an increase in cardiomyocyte cell division events (cytokinesis), cardiomyocytes were treated with individual microRNAs and additional markers were evaluated, namely: i) staining for histone H3 phosphorylated at Serine 10(P-S10-H3), which detects cells in late G2/mitosis; ii) staining for AuroraB kinase, a component of midbodies, a transient structure which appears near the end of cytokinesis just prior to, and is maintained for a brief period after, the complete separation of the dividing cells; and iii) cardiomyocyte number at 6 days after microRNA transfection.

Figure 4:
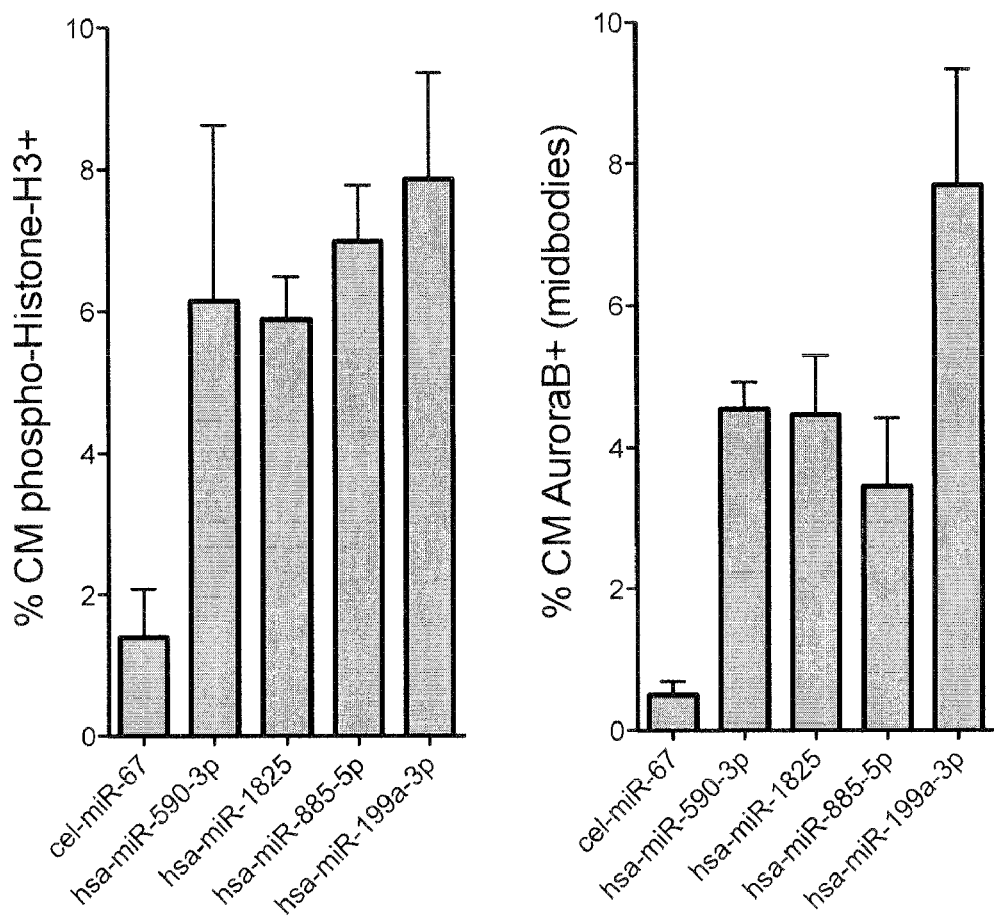
FIG. 4 shows examples of microRNAs increasing neonatal rat cardiomyocyte proliferation and cytokinesis in vitro, as evaluated by phosphorylation of histone H3 (left) and positivity for Aurora B localization in midbodies (right). cel-miR-67 is an ineffective microRNA used as control.

Treatment of cardiomyocytes with the selected microRNAs led to a significant increase in both the number of cells positive for P-S10-H3 (from 1.7% with control microRNA up to 8%) as well as the number of cells presenting midbodies (from 0.5% to 4%), as shown in FIG. 4. As expected, the percentages of cells positive for P-S10-H3 and midbodies were significantly smaller than those of Ki-67 and EdU, since the former are markers of events of relatively shorter duration.

Consistent with an efficient progression through the cell cycle and successful cytokinesis, analysis of cardiomyocytes treated with the selected microRNAs for 6 days revealed that the selected microRNAs also significantly increased the number of cardiomyocytes when compared to controls.

Methods

Selected individual microRNAs were transferred robotically into Primaria 96-well plates (BD Falcon). Transfection of the selected microRNAs into neonatal rat cardiomyocytes and immunofluorescence was performed as described in the Methods to Example 1. Cells were stained with the following primary antibodies: mouse monoclonal antibody against sarcomeric alpha-actinin (Abcam), rabbit antibody against histone H3 phosphorylated at Serine 10 (Millipore) and rabbit antibody against AuroraB kinase (Sigma).

Other reagents and procedures, including automated image acquisition and analysis, are the same as described in the Methods to Example 1. Quantification of midbodies stained with AuroraB antibody was performed by manual inspection and counting of the 1.6 images acquired per well.

Example 4

MicroRNAs Increase Proliferation of Fully Differentiated Adult Cardiomyocytes

A small percentage of cardiomyocytes isolated from newborn animals are still engaged in the cell cycle and able to proliferate (approximately 3-15% of cardiomyocytes, depending on the species) and therefore it could be envisaged that the microRNAs enhance the proliferative capacity of these cells.

To test whether the selected microRNAs, in addition to neonatal cardiomyocytes, might also induce re-entry into the cell cycle of fully differentiated cells, cardiomyocytes were isolated from adult (2-month old) rats and transfected with selected microRNAs. As an example, in FIG. 5 we show the effects of two of the selected microRNAs: hsa-miR-199a-3p and hsa-miR-590-3p (the microRNAs that performed best in inducing mouse and rat cardiomyocyte proliferation in vitro, respectively).

Remarkably, microRNA treatment determined a time-dependent re-entry of the cells into the cell cycle (from virtually none up to ca. 6% EdU+ cardiomyocytes for hsa-miR-590-3p and ca, 8% EdU+cardiomyocytes for hsa-miR-199a-3p at 7 days in culture), eventually leading to a significant increase of the number of cells in the plate.

These experiments dearly demonstrate that the microRNAs are able to induce proliferation not only of neonatal cardiac cells, but also of non-dividing, fully differentiated cardiomyocytes recovered from adult individuals.

Methods

Ventricular cardiomyocytes were isolated from Langendorff-perfused hearts of adult female Wistar rats (2-month old) as previously described (Xiao et al. 2001), with minor modifications. Briefly, hearts were extracted and perfused retrogradely with calcium-free Krebs-Henseleit bicarbonate (KHB) buffer. Hearts were then perfused with KHB buffer containing 1 mg/ml Liberase (Roche) for 10 min. Following removal of the atria and great vessels, the hearts were minced in KHB buffer and the cell mixture was filtered through a cell strainer (100 µm, BD Falcon). The cells were then pelleted by centrifugation at 530 g for 3 min at room temperature. The cell pellet was resuspended in a mixture DMEM 1.0 g/l glucose (Life Technologies) and perfusion buffer (1:1) and the separation of cardiomyocytes from other cell types was achieved by sedimentation on a 6% bovine serum albumin (BSA, Sigma) cushion for 15 min. The cardiomyocyte pellet was resuspended and plated in DMEM 1.0 g/l glucose supplemented with 2 g/l BSA, 2 mM L-carnitine (Sigma), 5 mM creatine (Sigma), 5 mM taurine (Sigma), 1 mM 2,3-butanedione monoxime (BDM; Sigma) and with 100 U/ml of penicillin and 100 µg/ml of streptomycin. Cells were plated on 24-well plates coated with laminin (Sigma), and kept at 37° C. in 5% CO2 and humidified atmosphere. The medium was exchanged 24 h later to DMEM 4.5 g/l glucose supplemented with 5% FBS, 20 µg/ml vitamin B12 and the cells were transfected as described below.

Transfection of rat cardiomyocytes isolated from adult animals was performed essentially as described in Methods to Example 1 for neonatal cardiomyocytes, except that transfections were performed 24 h after cell seeding using a forward transfection protocol at a final microRNA concentration of 50 nM. The medium was replaced by medium containing 5 µM EdU 48 h after transfection and every 24 h thereafter until the cells were fixed, 6 days after transfection.

Other reagents and procedures, including automated image acquisition and analysis, are the same as described in the Methods to Example 1.

Example 5

MicroRNAs Increase Cardiomyocyte Proliferation In Vivo

Given the observed increase in cardiomyocyte proliferation upon treatment with selected microRNAs in vitro, we wanted to determine whether these microRNAs would also increase proliferation in viva As an example, here we show the effects of two of the selected microRNAs: hsa-miR-199a-3p and hsa-miR-590-3p (the microRNAs that performed best in inducing mouse and rat cardiomyocyte proliferation in vitro, respectively).

The synthetic microRNAs, complexed with transfection reagent, were injected directly into the heart of neonatal rats, and their effect was evaluated 4 days later, by comparing the number of cells that incorporated EdU in animals injected with each of the two selected microRNAs to that of animals injected with a control microRNA (cel-miR-67). We observed a significant increase in the number of proliferating cells in the heart of animals injected with the selected microRNAs (from 3% in animals injected with cel-miR-67 to approximately 10% in animals injected with hsa-miR-199a-3p and hsa-miR-590-3p). Of notice, we confirmed by confocal fluorescence microscopy that a significant fraction of the proliferating cells were indeed cardiomyocytes. Significant results are shown in FIG. 6, where examples of microRNAs increasing cardiomyocyte proliferation in vivo, as evaluated by EdU positivity, are provided.

As an alternative to the use of synthetic microRNAs, additional experiments were performed by intraperitoneal (IP) injection of adeno-associated virus (AAV)-based vectors encoding for hsa-miR-199a and hsa-miR-590 into neonatal mice. Various serotypes of AAV vectors (for examples, AAV9, AAV8, AAV1 and AAV2, according to the route of administration) efficiently transduce the heart (Inagaki et al, 2006; Collesi et al. 2008); expression of the microRNAs from these vectors is driven by the constitutive CMV promoter. The proliferation of cells in the heart was evaluated 12 days after injection, by staining with antibodies against alpha-actinin and P-S10-H3 to detect cells undergoing late G2/mitosis. We observed a significant increase in the number of proliferating cardiomyocytes in the heart of animals injected with the selected microRNAs when compared to animals injected with control AAV.

Using these approaches we determined that the microRNAs selected on the basis of the in vitro studies described in Examples 1, 2 and 3 are able to significantly increase the proliferation of cardiomyocytes in vivo, in both neonatal rat and mice. Moreover, we demonstrated that these microRNAs are active irrespectively of whether they are introduced as synthetic mature sequences, or expressed from a viral vector.

Methods

Neonatal Wistar rats (post-natal day1) were anesthetized by cooling on an ice bed for 5 min. Lateral thoracotomy at the fourth intercostal space was performed by dissection of the intercostal muscles following skin incision. Following intracardiac injection of the microRNA complexes using an insulin syringe with incorporated 30-gauge needle (Roche), neonates were removed from the ice bed, thoracic wall and skin incisions were sutured. Neonates were then placed under a heat lamp and warmed for several minutes until recovery. The microRNA complexes were prepared my mixing the microRNA (ca. 2.8 µg of cel-miR-67, hsa-miR-590-3p or hsa-miR-199a-3p, Dharmacon Thermo Scientific) with Lipofectamine RNAimax transfection reagent (Invitrogen) for 30 min at room temperature. The total volume of the mix injected per rat heart was 30 µl.

For the production of the AAV vectors, the pre-hsa-miR-199a and pre-hsa-miR-590 plus upstream and downstream flanking sequences (total approx. 300 bp) were amplified from human genomic DNA isolated from HeLa cells using the QIAamp DNA mini kit (Qiagen), according to the manufacturers instructions. The amplified sequences were cloned in pZac vector.

Recombinant AAV vectors were obtained as described previously (Zentilin et al., 2001). Briefly, AAV vectors were generated in HEK293T cells, using a triple plasmid co-transfection for packaging (Gao et al, 2004). Viral stocks were obtained by $CsCl_2$ gradient centrifugation. Titration of AAV viral particles was performed by real-time PCR quantification of the number of viral genomes, as described previously (Sunblind et al, 2001); the viral preparations used in this work had titers between $1\times10^{12}$ and $1\times10^{13}$ viral genome (vg) per ml.

In the experiments using AAV vectors, neonatal CD1 mice (post-natal day1) were injected intraperitoneally, using an insulin syringe with incorporated 30-gauge needle (Roche), with AAV-LacZ, AAV-hsa-miR-199a or AAV-hsa-miR-590 at a dose of $1\times10^{11}$ vg per animal.

The hearts of the injected rats and mice were collected 4 and 12 days after injection, respectively, and briefly rinsed in PBS to remove residual blood from the ventricles. Hearts were fixed in 10% formalin at room temperature and routinely processed for paraffin embedding. Hematoxylin/eosin and Masson's trichrome staining were performed according to standard procedures, and analyzed for regular morphology and extent of fibrosis. For immunofluorescence staining, sample slices were deparaffinized and rehydrated, and processed as described in Example 1. The following primary antibodies were used: mouse monoclonal antibody against sarcomeric alpha-actinin (Abeam) and rabbit antibody against Histone H3 phosphorylated at Serine 10 (Millipore), followed by secondary antibody staining with anti-mouse and anti-rabbit secondary antibodies conjugated to Alexa Fluor 488 or 555 (Invitrogen). Nuclei were identified by counter-staining sections with TOTO-3 (Invitrogen). Slides were mounted in Vectashield with DAPI (Vector Labs) and imaged using an ImageXpress Micro automated high-content screening fluorescence microscope (Molecular Devices) or a laser confocal 510 META microscope (Carl Zeiss MicroImaging).

Quantification of EdU or P-S10-H3 positive cells in the different heart slices was performed by automated image analysis, as described in Examples 1 and 3.

Example 6

MicroRNAs Preserve Cardiac Function after Myocardial Infarction

Taking into consideration the observed increase in cardiomyocyte proliferation upon treatment with selected microRNAs in vitro and in vivo, we assessed the effect of the microRNAs on cardiac function after myocardial infarction in mice.

For this purpose, mice underwent permanent left anterior descending coronary artery ligation, immediately followed by injection into the left-ventricular pen-infarcted area of the AAV vectors expressing the selected microRNAs or control vector. As evaluated by echocardiography at 12 days and 1 month after myocardial infarction, the left ventricular ejection fraction (LVEF) and fractional shortening (LVFS) were significantly preserved in infarcted mice injected with AAV-hsa-miR-199a or AAV-hsa-miR-590, compared to animals treated with control AAV (at 1 month: LVEF 42%, 53%; 54%; LVFS 20%, 27%, 26% in control, hsa-miR-199a and hsa-miR-590 animals, respectively; P<0.05). The LV endsystolic wall thickening of the infarcted hearts injected with the AAV vectors expressing the selected microRNAs was also markedly improved when compared to the control group (from 077 mm in animals injected with control AAV to 0.98 and 0.97 mm in animals injected with AAV-hsa-miR-199a and AAV-hsa-miR-590, respectively).

To determine whether the improvement in cardiac function induced by the selected microRNAs correlates with a decrease in infarct size, a sub-group of the animals (n=6) was sacrificed at 12 days after myocardial infarction and the hearts were examined for post-infarction fibrosis. Analysis of trichromic-stained heart cross-sections showed that mice treated with MV-hsa-miR-199a and AAV-hsa-miR-590 had a significant reduction of the infarct size when compared to control infarcted mice (from 28% of LV area in animals injected with control AAV to 14% and 13% in animals injected with AAV-hsa-miR-199a and AAV-hsa-miR-590, respectively).

Together, these data indicate that expression of hsa-miR-199a and hsa-miR-590 in an animal model of myocardial infarction can reduce the infarct size and significantly improve cardiac function.

FIG. 7 shows the effects of microRNA hsa-miR-590-3p and microRNA hsa-miR-199a-3p upon delivery, using an AAV vector, to the heart of infarcted mice.

Methods

Myocardial infarction was produced in female CD1 mice (8-12 weeks old), by permanent left anterior descending (LAD) coronary artery ligation. Briefly, mice were anesthetized with an intraperitoneal injection of ketamine and xylazine, endotracheally intubated and placed on a rodent ventilator. Body temperature was maintained at 37° C. with a heating pad. The beating heart was accessed via a left thoracotomy. After removing the pericardium, a descending branch of the LAD coronary artery was visualized with a steromicroscope (Leica) and occluded with a nylon suture. Ligation was confirmed by the whitening of a left ventricular region immediately post-ligation. Recombinant AAV vectors at a dose of $1\times10^{11}$ vg per animal, produced as described in Example 5, were injected immediately after LAD ligation into the myocardium bordering the infarct zone (single injection), using an insulin syringe with incorporated 30-gauge needle (Roche). Three groups of animals were studied (n=12/group), receiving AAV-Lara, AAV-hsa-miR-199a, or AAV-hsa-miR-590. The chest was closed, and the animals moved to a prone position until the occurrence of spontaneous breathing.

To evaluate left ventricular function and dimensions, transthoracic two-dimensional echocardiography was performed 12 days and 1 month after myocardial infarction, in mice sedated with 5% isoflurane using a Visual Sonics Vevo 770 Ultrasound (Visual Sonics), equipped with a 30-MHz linear array transducer. M-mode tracings were used to measure left ventricular anterior and posterior wall thickness and internal diameter at end-systole and end-diastole, fractional shortening and ejection fraction.

At the end of the echocardiography study (12 days or 1 month after infarction), hearts were collected and processed for histology and immunofluorescence, as described in Example 5, Infarct size was measured as the fibrotic area as a percentage of total left ventricular area.

CITED REFERENCES

Ahuja, P., Sdek, P., and MacLellan, W. R. (2007), Cardiac myocyte cell cycle control in development, disease, and regeneration. Physiological reviews 87, 521-544.

Bartel, D. P. (2009), MicroRNAs: target recognition and regulatory functions. Cell 136, 215-233.

Bergmann, O., Bhardwaj, R. D., Bernard, S., Zdunek, S., Barnabe-Heider, F., Walsh, S., Zupicich, J., Alkass, K., Buchholz, B. A., Druid, H., et al. (2009). Evidence for cardiomyocyte renewal in humans. Science (New York, N.Y. 324, 98-102.

Bueno, M. J., Perez de Castro, I., and Malumbres, M. (2008). Control of cell proliferation pathways by microRNAs. Cell cycle (Georgetown, Tex. 7, 3143-3148.

Callis, T. E., Pandya, K., Seok, H. Y., Tang, R. H., Tatsuguchi, M., Huang, Z. P., Chen, J. F., Deng, Z., Gunn, B., Shumate, J., et al. (2009). MicroRNA-208a is a regulator of cardiac hypertrophy and conduction in mice. The Journal of clinical investigation 119, 2772-2786.

Care, A., Catalucci, D., Felicetti, F., Bonci, D., Addario, A., Gallo, P., Bang, M. L., Segnalini, P., Gu, Y., Dalton, N. D., et (2007). MicroRNA-133 controlscardiachypertrophy. Nature medicine 13, 613-618.

Chen, J. F., Murchison, E. P., Tang, R., Callis, T. E., Tatsuguchi, M., Deng, Z., Rojas, M., Hammond, S. M., Schneider, M. D., Selzman, C. H., et al. (2008), Targeted deletion of Dicer in the heart leads to dilated cardiomyopathy and heart failure. Proceedings of the National Academy of Sciences of the United States of America 105, 2111-2116.

Collesi, C., Zentilin, L., Sinagra, G., and Giacca, M. (2008). Notch1 signaling stimulates proliferation of immature cardiomyocytes. The Journal of cell biology 183, 117-128.

Croce, C. M. (2009). Causes and consequences of microRNA dysregulation in cancer. Nature reviews 10, 704-714.

Elmen, J., Lindow, M., Schutz, S., Lawrence, M., Petri, A., Obad, S., Lindholm, M., Hedtjarn, M., Hansen, H. F., Berger, U., et al. (2008). LNA-mediated microRNA silencing in non-human primates. Nature 452, 896-899.

Eulalio, A., Huntzinger, E., and Izaurralde, E. (2008). Getting to the root of miRNA-mediated gene silencing. Cell 132, 9-14.

Filipowicz, W., Bhattacharyya, S. N., and Sonenberg, N. (2008). Mechanisms of post-transcriptional regulation by microRNAs: are the answers in sight? Nature reviews 9, 102-114.

Gao, G., Vandenberghe, L. H., Alvira, M. R., Lu, Y., Calcedo, R., Zhou, X., and Wilson, J. M. (2004). Clades of Adeno-associated viruses are widely disseminated in human tissues. Journal of virology 78, 6381-6388.

Ghildiyal, M., and Zamore, P. D. (2009). Small silencing RNAs: an expanding universe. Nature reviews 10, 94-108.

Hu, S., Huang, M., Li, Z., Jia, F., Ghosh, Z., Lijkwan, M., Fasanaro, P., Sun, S., Wang, X., Martelli, F., Robbins, R. C., Wu, J., MicroRNA-210 as a Novel Therapy for Treatment of Ischemic Heart Disease, Circulation 2010 Sep. 14; 122(11 Suppl.): S124-S131.

Huang, Z. P., Neppl, R. L., and Wang, D. Z. (2010). MicroRNAs in cardiac remodeling and disease. Journal of cardiovascular translational research 3, 212-218.

Ikeda, S., Kong, S. W., Lu, J., Bisping, E., Zhang, H., Allen, P. D., Golub, T. R., Pieske, B., and Pu, W. T. (2007). Altered microRNA expression in human heart disease. Physiological genomics 31, 367-373.

Inagaki, K., Fuess, S., Storm, T. A., Gibson, G. A., McTiernan, C. F., Kay, M. A., and Nakai, H. (2006). Robust systemic transduction with AAV9 vectors in mice: efficient global cardiac gene transfer superior to that of AAV8. Mol Ther 14, 45-53.

Kedde, M., and Agami, R. (2008). Interplay between microRNAs and RNA-binding proteins determines developmental processes. Cell cycle (Georgetown, Tex. 7, 899-903.

Lanford, R. E., Hildebrandt-Eriksen, E. S., Petri, A., Persson, R., Lindow, M., Munk, M. E., Kauppinen, S., and Orum, H. (2010). Therapeutic silencing of microRNA-122 in primates with chronic hepatitis C virus infection, Science (New York, N.Y. 327, 198-201.

Latronico, M. V., and Condorelli, G. (2009). MicroRNAs and cardiac pathology. Nat Rev Cardiol 6, 419-429.

Lin, Z., Murtaza, I., Wang, K., Jiao, 1, Gao, 3., and Li, P. F. (2009). miR-23a functions downstream of NFATc3 to regulate cardiac hypertrophy. Proceedings of the National Academy of Sciences of the United States of America 106, 12103-12108, Liu, N., Williams, A. H., Kim, Y., McAnally, J., Bezprozvannaya, S., Sutherland, L. B., Richardson, J. A., Basset-Duby, R., and Olson, E. N. (2007), An intragenic MEF2-dependent enhancer directs muscle-specific expression of microRNAs 1 and 133. Proceedings of the Nation& Academy of Sciences of the United States of America 104, 20844-20849, Matkovich, S. J., Van Booven, D. J., Youker, K. A., Torre-Amione, G., Diwan, A., Eschenbacher, W. H., Dorn, L. E., Watson, M. A., Margulies, K. B., and Dorn, G. W., 2nd (2009). Reciprocal regulation of myocardial microRNAs and messenger RNA in human cardiomyopathy and reversal of the microRNA signature by biomechanical support. Circulation 119, 12634271.

Mingozzi F, High K A. Therapeutic in vivo gene transfer for genetic disease using AAV: progress and challenges. Nat Rev Genet 2011; 12: 341-355.

Najafi-Shoushtari, S. H., Krista, F., Li, Y., Shioda, T., Cohen, D. E., Gerszten, R. E., and Naar, A. M. (2010), MicroRNA-33 and the SREBP host genes cooperate to control cholesterol homeostasis. Science (New York, N.Y. 328, 1566-1569.

O'Connell, R. M., Rao, D. S., Chaudhuri, A. A., and Baltimore, D, (2010). Physiological and pathological roles for microRNAs in the immune system. Nat Rev Immunol 10, 111-122.

Porrello, E. R., Johnson, B. A., Aurora, A. B., Simpson, E., Nam, Y. J., Matkovich, S. J., Dorn, G. W., 2nd, van Rooij, E., and Olson, E. N. (2011). MiR-15 family regulates postnatal mitotic arrest of cardiomyocytes. Circulation research 109, 670-679.

Rao, P. K., Toyama, Y., Chiang, H. R., Gupta, S., Bauer, M., Medvid, R., Reinhardt, F., Liao, R., Krieger, M., Jaenisch, R., et al. (2009). Loss of cardiac microRNA-mediated regulation leads to dilated cardiomyopathy and heart failure. Circulation research 105, 585-594.

Senyo, S. E., Steinhauser, Pizzimenti, C. L., Yang, V. K., Cai, L., Wang, M., Wu, T. D., Guerquin-Kern, J. L., Lechene, C. P., Lee, R. T. 2012. *Mammalian heart renewal by pre-existing cardiomyocytes*. Nature, in press Small, E. M., Frost, R. J., and Olson, E. N. (2010). MicroRNAs add a new dimension to cardiovascular disease. Circulation 121, 1022-1032, Small, E. M., and Olson, E. N. Pervasive roles of microRNAs in cardiovascular biology. Nature 469, 336-342.

Thum, T., Galuppo, P., Wolf, C., Fiedler, J., Kneitz, S., van Laake, L. W., Doevendans, P. A., Mummery, C. L., Borlak, J., Haverich, A., et al. (2007), MicroRNAs in the human heart: a clue to fetal gene reprogramming in heart failure. Circulation 116, 258267.

Thum, T., Gross, C., Fiedler, J., Fischer, T., Kissler, S., Bussen, M., Galuppo, P., Just, S., Rottbauer, W., Frantz, S., et al. (2008). MicroRNA-21 contributes to myocardial disease by stimulating MAP kinase signaling in fibroblasts. Nature 456, 980-984.

Umbach, J. L., and Cullen, B. R. (2009). The role of RNAi and microRNAs in animal virus replication and antiviral immunity. Genes & development 23, 1151-1164. van Amerongen, M. J., and Engel, F. B. (2008). Features of cardiomyocyte proliferation and its potential for cardiac regeneration. Journal of cellular and molecular medicine 12, 2233-2244.

van Rooij, E., and Olson, E. N. (2007). MicroRNAs: powerful new regulators of heart disease and provocative therapeutic targets, The Journal of clinical investigation 117, 2369-2376.

van Rooij, E., Sutherland, L. B., Liu, N., Williams, A. H., McAnally, J., Gerard, R. D., Richardson, J. A., and Olson, E. N. (2006), A signature pattern of stress-responsive microRNAs that can evoke cardiac hypertrophy and heart failure. Proceedings of the National Academy of Sciences of the United States of America 103, 18255-18260.

van Rooij, E., Sutherland, L. B., Qi, X., Richardson, J. A., Hill, 3., and Olson, E. N. (2007). Control of stress-dependent cardiac growth and gene expression by a microRNA. Science (New York, N.Y. 316, 575-579.

van Rooij, E., Sutherland, L. B., Thatcher, J. E., DiMaio, J. M., Naseem, R. H., Marshall, W. S., Hill, J. A., and Olson, E. N. (2008). Dysregulation of microRNAs after myocardial infarction reveals a role of miR-29 in cardiac fibrosis. Proceedings of the National Academy of Sciences of the United States of America 105, 1302743032.

Williams, A. H., Liu, N., van Rood, E., and Olson, E. N. 2009). MicroRNA control of muscle development and disease. Current opinion in cell biology 21, 461-469.

Xiao, L., Pimental, D. R., Amin, J. K., Singh, K, Sawyer, D. B., Colucci, W. S. 2001. MEK1/2-ERK1/2 mediates alpha1-adrenergic receptor-stimulated hypertrophy in adult rat ventricular myocytes. J Mol Cell Cardiol 33, 779-87, Yang, B., Lin, H., Xiao, J., Lu, Y., Luo, X., Li, B., Zhang, Y., Xu, C., Bai, Y., Wang, H., et al. (2007). The muscle-specific microRNA miR-1 regulates cardiac arrhythmogenic potential by targeting GJA1 and KCNJ2. Nature medicine 13, 486-491.

Zentilin, L., Marcello, A., and Giacca, M. (2001). Involvement of cellular double-stranded DNA break binding proteins in processing of the recombinant adeno-associated virus genome. Journal of virology 75, 12279-12287.

Zhao, V., Samal, E., and Srivastava, D. (2005). Serum response factor regulates a muscle-specific microRNA that targets Hand2 during cardiogenesis. Nature 436, 214-220.

The invention claimed is:

1. A method for treatment of myocardial infarction, ischemic and non-ischemic cardiomyopathy, myocarditis or heart failure, comprising administering a microRNA selected from the group consisting of:
- hsa-miR-1825 (SEQ ID NO: 35);
- hsa-miR-33b*(SEQ ID NO: 10);
- hsa-miR-1248 (SEQ ID NO: 33),
  - or a primary transcript for such microRNA, or a precursor of such microRNA, or a mimic of such microRNA or a combination thereof.

2. The method according to claim 1, performed by gene therapy.

3. The method according to claim 1, wherein the mimic of such microRNA comprises one or more synthetic nucleic acids or modifications of microRNA backbone selected from the group consisting of: substitution of non-bonding oxygen atoms in a phosphate group, introduction of an alkyl group in a sugar molecule of nucleotides, and/or inclusion of extra bonds connecting carbon or oxygen atoms in sugars of nucleotides.

4. The method of claim 1, wherein the microRNA, or a primary transcript, precursor or mimic thereof, is administered together with lipidic molecules.

5. A method for treatment of myocardial infarction, ischemic and non-ischemic cardiomyopathy, myocarditis or heart failure, comprising administering a vector comprising at least a microRNA consisting of one sequence selected from the group consisting of SEQ ID NOs: 35, 10, and 33 or a primary transcript for said microRNA, or a precursor for said microRNA, or a mimic of said microRNA, or a combination thereof;
and/or a DNA coding for at least said microRNA and/or a DNA coding for at least a primary transcript or a precursor for said microRNA, or a combination thereof.

6. The method according to claim 5, wherein said vector is an adeno-associated vector (AAV) of any capsid serotype, either natural or artificial.

7. The method according to claim 5, wherein the mimic of said microRNA comprises one or more synthetic nucleic acids or modifications of microRNA backbone selected from the group consisting of: substitution of non-bonding oxygen atoms in a phosphate group, introduction of an alkyl group in a sugar molecule of nucleotides, and/or inclusion of extra bonds connecting carbon or oxygen atoms in sugars of nucleotides.

8. The method of claim 5, wherein the vector is administered together with lipidic molecules.

9. A method for treatment of myocardial infarction, ischemic and non-ischemic cardiomyopathy, myocarditis or heart failure, comprising administering a pharmaceutical composition comprising at least a microRNA consisting of one sequence selected from the group consisting of SEQ ID NOs: 35, 10, and 33 and/or a primary transcript of said microRNA, and/or a precursor of said microRNA, and/or a DNA coding for at least said microRNA, primary transcript, or precursor; and/or a mimic of at least said microRNA; or a combination thereof; and at least one pharmaceutically acceptable vehicle or excipient.

10. The method according to claim 9, wherein the administration is selected from the group consisting of parenteral, intravenous, intracoronary, and intracardiac administration.

11. The method according to claim 9, wherein said composition further comprises lipidic molecules, peptides, polymers, and other carrier molecules.

12. The method according to claim 9, wherein said composition further comprises cationic lipids.

13. The method according to claim 9, wherein the mimic of said microRNA comprises one or more synthetic nucleic acids or modifications of microRNA backbone selected from the group consisting of: substitution of non-bonding oxygen atoms in a phosphate group, introduction of an alkyl group in a sugar molecule of nucleotides, and/or inclusion of extra bonds connecting carbon or oxygen atoms in sugars of nucleotides.

14. A method for treatment of myocardial infarction, ischemic and non-ischemic cardiomyopathy, myocarditis or heart failure, comprising:
(a) obtaining an RNA stretch comprising at least one or a combination of microRNAs consisting of one sequence selected from the group consisting of SEQ ID NOs: 35, 10, and 33 or primary transcripts, precursors, or mimics of the at least one or a combination of microRNAs; and
(b) administering to a subject with myocardial infarction, ischemic and non-ischemic cardiomyopathy, myocarditis or heart failure said RNA stretch.

15. The method according to claim 14, wherein the mimic of said microRNA comprises one or more synthetic nucleic acids or modifications of microRNA backbone selected from the group consisting of: substitution of non-bonding oxygen atoms in a phosphate group, introduction of an alkyl group in a sugar molecule of nucleotides, and/or inclusion of extra bonds connecting carbon or oxygen atoms in sugars of nucleotides.

16. The method of claim 14, wherein the RNA stretch is administered together with lipidic molecules.

17. The method of claim 4, wherein the lipidic molecules are cationic lipids.

18. The method of claim 1, wherein the microRNA, or a primary transcript, precursor or mimic thereof is administered together with a peptide or polymer.

* * * * *